US011085044B2

(12) United States Patent
Guo et al.

(10) Patent No.: US 11,085,044 B2
(45) Date of Patent: *Aug. 10, 2021

(54) MIRNA FOR TREATMENT OF BREAST CANCER

(71) Applicant: UNIVERSITY OF KENTUCKY RESEARCH FOUNDATION, Lexington, KY (US)

(72) Inventors: Peixuan Guo, Columbus, OH (US); Dan Shu, Columbus, OH (US); Yi Shu, Columbus, OH (US); Hui Li, Columbus, OH (US); Farzin Haque, Long Island City, NY (US)

(73) Assignee: UNIVERSITY OF KENTUCKY RESEARCH FOUNDATION, Lexington, KY (US)

(*) Notice: Subject to any disclaimer, the term of this patent is extended or adjusted under 35 U.S.C. 154(b) by 0 days.

This patent is subject to a terminal disclaimer.

(21) Appl. No.: 15/555,822

(22) PCT Filed: Mar. 9, 2016

(86) PCT No.: PCT/US2016/021451
§ 371 (c)(1),
(2) Date: Sep. 5, 2017

(87) PCT Pub. No.: WO2016/145008
PCT Pub. Date: Sep. 15, 2016

(65) Prior Publication Data
US 2019/0119682 A1 Apr. 25, 2019

Related U.S. Application Data

(60) Provisional application No. 62/175,774, filed on Jun. 15, 2015, provisional application No. 62/130,533, filed on Mar. 9, 2015.

(51) Int. Cl.
| | |
|---|---|
| *C07H 21/04* | (2006.01) |
| *A61K 48/00* | (2006.01) |
| *C12N 15/113* | (2010.01) |
| *C12N 15/115* | (2010.01) |
| *C07H 21/02* | (2006.01) |
| *A61P 35/00* | (2006.01) |
| *A61K 9/51* | (2006.01) |
| *B82Y 5/00* | (2011.01) |

(52) U.S. Cl.
CPC ............ *C12N 15/1135* (2013.01); *A61K 9/51* (2013.01); *A61P 35/00* (2018.01); *C07H 21/02* (2013.01); *C12N 15/113* (2013.01); *C12N 15/115* (2013.01); *C12N 15/1138* (2013.01); *B82Y 5/00* (2013.01); *C12N 2310/11* (2013.01); *C12N 2310/12* (2013.01); *C12N 2310/14* (2013.01); *C12N 2310/141* (2013.01); *C12N 2310/16* (2013.01); *C12N 2310/52* (2013.01); *C12N 2320/30* (2013.01)

(58) Field of Classification Search
CPC .. C12N 15/113; C12N 15/115; C12N 2310/14
See application file for complete search history.

(56) References Cited

U.S. PATENT DOCUMENTS

| | | |
|---|---|---|
| 6,180,082 B1 | 1/2001 | Woltering et al. |
| 6,506,559 B1 | 1/2003 | Fire et al. |
| 2008/0213177 A1 | 9/2008 | Rademacher et al. |
| 2009/0143326 A1 | 6/2009 | Obad et al. |
| 2010/0203142 A1 | 8/2010 | Zhang et al. |
| 2011/0014715 A1 | 1/2011 | Lee et al. |
| 2011/0077288 A1* | 3/2011 | Kauppinen .......... C12N 15/113 514/44 R |
| 2012/0214864 A1 | 8/2012 | Richer et al. |
| 2013/0177556 A1 | 7/2013 | De Franciscis et al. |
| 2014/0017958 A1 | 1/2014 | Nemoto |
| 2014/0045709 A1 | 2/2014 | Croce et al. |
| 2014/0179758 A1 | 6/2014 | Guo |

FOREIGN PATENT DOCUMENTS

| | | |
|---|---|---|
| WO | 1999/07409 | 2/1999 |
| WO | 1999/032619 | 7/1999 |
| WO | 2000/001846 | 1/2000 |
| WO | 2000/044895 | 8/2000 |
| WO | 2000/044914 | 8/2000 |
| WO | 2001/029058 | 4/2001 |
| WO | 2001/036646 | 5/2001 |
| WO | WO 2007/016507 A2 * | 2/2007 ........... C12N 15/113 |

(Continued)

OTHER PUBLICATIONS

Zhang et al. (RNA, 19, 2013, 1226-1237).*
Shu et al. (Methods, 54, 2011, 204-214).*
Guo et al. (Gene Ther, 2006, 13(10), 814-820).*
Yan et al. (Breast Cancer Res, 2011, 13(1), R2).*
ISR dated Aug. 26, 2016.
Written Opinion of the ISA dated Aug. 26, 2016.
Lee, J. B.; Hong, J.; Bonner, D. K.; Poon, Z.; Hammond, P. T. Self-Assembled RNA Interference Microsponges for Efficient SiRNA Delivery. Nat. Mater. 2012, 11, 316-322.
Lee, T. J.; Hague, F.; Shu, D.; Yoo, J. Y.; Li, H.; Yokel, R. A.; Horbinski, C.; Kim, T. H.; Kim, S.-H.; Nakano, I.; Kaur, B.; Croce, C. M.; Guo, P. RNA Nanopartides as a Vector for Targeted SiRNA Delivery into Glioblastoma Mouse Model. Oncotarget 2015, (In Press).

(Continued)

*Primary Examiner* — Amy H Bowman
(74) *Attorney, Agent, or Firm* — Baker Donelson

(57) ABSTRACT

The presently-disclosed subject matter relates to RNA-based composition and method to treat breast cancer in a subject. More particularly, the presently disclosed subject matter relates to a RNA nanostructure and composition containing a multiple branched RNA nanoparticle, a breast cancer targeting module, and an effective amount of a breast cancer therapeutic agent. Further, the presently disclosed subject matter relates to a method of using the RNA nanoparticle composition to treat breast cancer in a subject having or at risk of having breast cancer.

34 Claims, 3 Drawing Sheets

Specification includes a Sequence Listing.

(56) References Cited

FOREIGN PATENT DOCUMENTS

| WO | 2010/017515 | 2/2010 | |
|---|---|---|---|
| WO | WO 2012/049112 A1 * | 4/2012 | ........... C12N 15/113 |

OTHER PUBLICATIONS

Li, H.; Rychahou, P. G.; Cui, Z.; Pi, F.; Evers, B. M.; Shu, D.; Guo, P.; Luo, W. RNA Nanoparticles Derived From Three-Way Junction of Phi29 Motor PRNA Are Resistant to 1-125 and Cs-131 Radiation. Nucleic Acid Ther. 2015.

Liang, Z.; Wang, X. J. Rising From Ashes: Non-Coding RNAs Come of Age. J Genet. Genomics 2013, 40, 141-142.

Liu, J.; Guo, S.; Cinier, M.; Shlyakhtenko, L. S.; Shu, Y.; Chen, C.; Shen, G.; Guo, P. Fabrication of Stable and RNase-Resistant RNA Nanoparticles Active in Gearing the Nanomotors for Viral DNA Packaging. ACS Nano 2011, 5, 237-246.

Longmire, M.; Choyke, P. L.; Kobayashi, H. Clearance Properties of Nano-Sized Particles and Molecules as Imaging Agents: Considerations and Caveats. Nanomedicine (Lond) 2008, 3, 703-717.

Lyubchenko, Y. L.; Gall, A. A.; Shlyakhtenko, L. S.; Harrington, R. E.; Jacobs, B. L.; Oden, P. I.; Lindsay, S. M. Atomic Force Microscopy Imaging of Double Stranded DNA and RNA. J. Biomol. Struct. Dyn. 1992, 10, 589-606.

Lyubchenko, Y. L.; Shlyakhtenko, L. S. AFM for Analysis of Structure and Dynamics of DNA and Protein-DNA Complexes. Methods 2009, 47, 206-213.

Lyubchenko, Y. L.; Shlyakhtenko, L. S.; Ando, T. Imaging of Nucleic Acids With Atomic Force Microscopy. Methods 2011, 54, 274-283.

Mathe, C.; Perigaud, C. Recent Approaches in the Synthesis of Conformationally Restricted Nucleoside Analogues. Eur. J. Org. Chem. 2008, 1489-1505.

Morrissey, D. V.; Lockridge, J. A.; Shaw, L.; Blanchard, K.; Jensen, K.; Breen, W.; Hartsough, K.; Machemer, L.; Radka, S.; Jadhav, V.; et al. Potent and Persistent in vivo Anti-HBV Activity of Chemically Modified siRNAs. Nat. Biotechnol. 2005, 23, 1002-1007.

Obad, S.; dos Santos, C. O.; Petri, A.; Heidenblad, M.; Broom, O.; Ruse, C.; Fu, C.; Lindow, M.; Stenvang, J.; Straarup, E. M.; et al. Silencing of MicroRNA Families by Seed-Targeting Tiny LNAs. Nat. Genet. 2011, 43, 371-378.

Pantel, K.; Brakenhoff, R. H.; Brandt, B. Detection, Clinical Relevance and Specific Biological Properties of Disseminating Tumour Cells. Nat Rev. Cancer 2008, 8, 329-340.

Peer, D.; Karp, J. M.; Hong, S.; Farokhzad, O. C.; Margalit, R.; Langer, R. Nanocarriers as an Emerging Platform for Cancer Therapy. Nat Nanotechnol. 2007, 2, 751-760.

Qi, L.; Bart, J.; Tan, L. P.; Platted, I.; Sluis, T.; Huitema, S.; Harms, G.; Fu, L.; Hollema, H.; Berg, A. Expression of MiR-21 and Its Targets (PTEN, PDCD4, TM1) in Flat Epithelial Atypia of the Breast in Relation to Ductal Carcinoma in situ and Invasive Carcinoma. BMC. Cancer 2009, 9, 163.

Redzic, J. S.; Balaj, L.; van der Vos, K. E.; Breakefield, X. O. Extracellular RNA Mediates and Marks Cancer Progression. Semin. Cancer Biol. 2014, 28, 14-23.

Robinson, R. RNAi Therapeutics: How Likely, How Soon? Plos Biology 2004, 2, e28. Shopsowitz, K. E.; Roh, Y. H.; Deng, Z. J.; Morton, S. W.; Hammond, P. T. RNAi-Microsponges Form Through Self-Assembly of the Organic and Inorganic Products of Transcription. Small 2014, 10, 1623-1633.

Shopsowitz, K. E.; Roh, Y. H.; Deng, Z. J.; Morton, S. W.; Hammond, P. T. RNAi-Microsponges Form Through Self-Assembly of the Organic and Inorganic Products of Transcription. Small 2014, 10, 1623-1633.

Shu, D.; Shu, Y.; Haque, F.; Abdelmawla, S.; Guo, P. Thermodynamically Stable RNA Three-Way Junctions for Constructing Multifuntional Nanoparticles for Delivery of Therapeutics. Nat. Nanotechnol. 2011, 6, 658-667.

Shu, D.; Zhang, L.; Khisamutdinov, E.; Guo, P. Programmable Folding of Fusion RNA Complex Driven by the 3WJ Motif of Phi29 Motor PRNA. Nucleic Acids Res. 2013, 42, e10.

Shu, Dan et al., (2015) ACS Nano, vol. 9, No. 10, 9731-9740.

Shu, Y.; Haque, F.; Shu, D.; Li, W.; Zhu, Z.; Kotb, M.; Lyubchenko, Y.; Guo, P. Fabrication of 14 Different RNA Nanopartides for Specific Tumor Targeting Without Accumulation in Normal Organs. RNA 2013, 19, 766-777.

Shu, Y.; Pi, F.; Sharma, A.; Rajabi, M.; Haque, F.; Shu, D.; Leggas, M.; Evers, B. M.; Guo, P. Stable RNA Nanopartides as Potential New Generation Drugs for Cancer Therapy. Adv. Drug Deliv. Rev. 2014, 66C, 74-89.

Si, M. L.; Zhu, S.; Wu, H.; Lu, Z.; Wu, F.; Mo, Y. Y. MiR-21-Mediated Tumor Growth. Oncogene 2007, 26, 2799-2803.

Srivastava, A.; Filant, J.; Moxley, K. M.; Sood, A.; McMeekin, S.; Ramesh, R. Exosomes: A Role for Naturally Occurring Nanovesicles in Cancer Growth, Diagnosis and Treatment. Current gene therapy 2014.

Tabernero, J.; Shapiro, G. I.; Lorusso, P. M.; Cervantes, A.; Schwartz, G. K.; Weiss, G. J.; Paz-Ares, L.; Cho, D. C.; Infante, J. R.; Alsina, M.; et al. First-in-Man Trial of an RNA Interference Therapeutic Targeting VEGF and KSP in Cancer Patients With Liver Involvement. Cancer Discov. 2013, 3, 406-417.

Takahashi, M.; Yamada, N.; Hatakeyama, H.; Murata, M.; Sato, Y.; Minakawa, N.; Harashima, H.; Matsuda, A. In vitro Optimization of 2'-OMe-4'-Thioribonucleoside-Modified Anti-MicroRNA Oligonucleotides and Its Targeting Delivery to Mouse Liver Using a Liposomal Nanoparticle. Nucleic Acids Res 2013, 41, 10659-10667.

Tiemann, K.; Rossi, J. J. RNAi-Based Therapeutics-Current Status, Challenges and Prospects. EMBO Mol. Med. 2009, 1, 142-151.

Wu, S. Y.; Lopez-Berestein, G.; Calin, G. A.; Sood, A. K. Targeting the undrggable: Advances and obstacles in current RNAi therapy. Sci. Transl. Med. 2014, 6, 240ps7.

Zhang, H. G.; Grizzle, W. E. Exosomes: A Novel Pathway of Local and Distant Intercellular Communication That Facilitates the Growth and Metastasis of Neoplastic Lesions. The American journal of pathology 2014, 184, 28-41.

Zhang, H.; Endrizzi, J. A.; Shu, Y.; Haque, F.; Sauter, C.; Shlyakhtenko, L. S.; Lyubchenko, Y.; Guo, P.; Chi, Y. I. Crystal Structure of 3WJ Core Revealing Divalent Ion-Promoted Thermostability and Assembly of the Phi29 Hexameric Motor PRNA. RNA 2013, 19, 1226-1237.

Zhang, Y.; Wang, Z.; Gemeinhart, R. A. Progress in MicroRNA Delivery. J Control Release 2013, 172, 962-974.

Zhu, S.; Si, M. L.; Wu, H.; Mo, Y. Y. MicroRNA-21 Targets the Tumor Suppressor Gene Tropomyosin 1 (TPM1). J. Biol Chem. 2007, 282, 14328-14336.

Zhu, S.; Wu, H.; Wu, F.; Nie, D.; Sheng, S.; Mo, Y. Y. MicroRNA-21 Targets Tumor Suppressor Genes in Invasion and Metastasis. Cell Res 2008, 18, 350-359.

Aagaard, L.; Rossi, J. J. RNAi Therapeutics: Principles, Prospects and Challenges. Adv. Drug Delivery Rev. 2007, 59, 75-86.

Abdelmawla, S.; Guo, S.; Zhang, L.; Pulukuri, S.; Patankar, P.; Conley, P.; Trebley, J.; Guo, P.; Li, Q. X. Pharmacological Characterization of Chemically Synthesized Monomeric PRNA Nanoparticles for Systemic Delivery. Mol. Ther. 2011, 19, 1312-1322.

Abels, J. A.; Moreno-Herrero, F.; van der Heijden, T.; Dekker, C. F.; Dekker, N. H. Single-Molecule Measurements of the Persistence Length of Double-Stranded RNA. Biophys. J. 2005, 88, 2737-2744.

Afonin, K. A.; Grabow, W. W.; Walker, F. M.; Bindewald, E.; Dobrovolskaia, M. A.; Shapiro, B. A.; Jaeger, L. Design and Self-Assembly of SiRNA-Functionalized RNA Nanoparticles for Use in Automated Nanomedicine. Nat Protoc. 2011, 6, 2022-2034.

Afonin, K. A.; Kireeva, M.; Grabow, W. W.; Kashlev, M.; Jaeger, L.; Shapiro, B. A. Co-Transcriptional Assembly of Chemically Modified RNA Nanoparticles Functionalized With SiRNAs. Nano. Lett. 2012, 12, 5192-5195.

Afonin, K. A.; Viard, M.; Koyfman, A. Y.; Martins, A. N.; Kasprzak, W. K.; Panigaj, M.; Desai, R.; Santhanam, A.; Grabow, W. W.; Jaeger, L.; et al. Multifunctional RNA Nanoparticles. Nano Lett. 2014, 14, 5662-5671.

(56) References Cited

OTHER PUBLICATIONS

Babar, I. A.; Cheng, C. J.; Booth, C. J.; Liang, X.; Weidhaas, J. B.; Saltzman, W. M.; Slack, F. J. Nanoparticle-Based Therapy in an in vivo MicroRNA-155 (MiR-155)-Dependent Mouse Model of Lymphoma. Proc. Natl. Acad. Sci. U. S A 2012, 109, E1695-E1704.
Bartel, D. P. MicroRNAs: Genomics, Biogenesis, Mechanism, and Function. Cell 2004, 116, 281-297.
Bass, Nature 411:428-429, 2001.
Behlke, M. A. Chemical Modification of siRNAs for in vivo Use. Oligonudeotides. 2008, 18, 305-319.
Binzel, D. W.; Khisamutdinov, E. F.; Guo, P. Entropy-Driven One-Step Formation of Phi29 PRNA 3WJ From Three RNA Fragments. Biochemistry 2014, 53, 2221-2231.
Bora, R. S.; Gupta, D.; Mukkur, T. K.; Saini, K. S. RNA Interference Therapeutics for Cancer: Challenges and Opportunities (Review). Mol. Med. Rep. 2012, 6, 9-15.
Bumcrot, D.; Manoharan, M.; Koteliansky, V.; Sah, D. W. RNAi Therapeutics: a Potential New Class of Pharmaceutical Drugs. Nat Chem. Biol. 2006, 2, 711-719.
Calin, G. A.; Croce, C. M. MicroRNA Signatures in Human Cancers. Nat. Rev. Cancer 2006, 6, 857-866.
Castoldi, M.; Schmidt, S.; Benes, V.; Hentze, M. W.; Muckenthaler, M. U. MiChip: an Array-Based Method for MicroRNA Expression Profiling Using Locked Nucleic Acid Capture Probes. Nat Protoc. 2008, 3, 321-329.
Cheng, C. J.; Saltzman, W. M. Polymer Nanoparticle-Mediated Delivery of MicroRNA Inhibition and Alternative Splicing. Mol Pharm. 2012, 9, 1481-1488.
Croce, C. M. Causes and Consequences of MicroRNA Dysregulation in Cancer. Nat Rev. Genet 2009, 10, 704-714.
Croce, C. M.; Calin, G. A. MiRNAs, Cancer, and Stem Cell Division. Cell 2005, 122, 6-7.
Di Leva, G.; Garofalo, M.; Croce, C. M. MicroRNAs in Cancer. Annu. Rev. Pathol. 2014, 9, 287-314.
Dibrov, S. M.; McLean, J.; Parsons, J.; Hermann, T. Self-Assembling RNA Square. Proc. Natl. Acad. Sci. U. S. A 2011, 108, 6405-6408.
Elbashir et al., Nature 411:494-498, 2001a.
Eldh, M.; Olofsson Bagge, R.; Lasser, C.; Svanvik, J.; Sjostrand, M.; Mattsson, J.; Lindner, P.; Choi, D. S.; Gho, Y.; Lotvall, J. MicroRNA in Exosomes Isolated Directly From the Liver Circulation in Patients With Metastatic Uveal Melanoma. BMC Cancer 2014, 14, 962.
Esposito, C. L.; Passaro, D.; Longobardo, I.; Condorelli, G.; Marotta, P.; Affuso, A.; de, F., V; Cerchia, L. A Neutralizing RNA Aptamer Against EGFR Causes Selective Apoptotic Cell Death. PLoS One 2011, 6, e24071.
Fadare, O.; Tavassoli, F. A. Clinical and Pathologic Aspects of Basal-Like Breast Cancers. Nat. Clin. Pract. Oncol. 2008, 5, 149-159.
Fire, A.; Xu, S.; Montgomery, M. K.; Kostas, S. A.; Driver, S. E.; Mello, C. C. Potent and Specific Genetic Interference by Double-Stranded RNA in Caenorhabditis Elegans. Nature 1998, 391, 806-811.
Fire, Trends Genet 15:358-363, 1999.
Foulkes, W. D.; Smith, I. E.; Reis-Filho, J. S. Triple-Negative Breast Cancer. N. Engl. J Med. 2010, 363, 1938-1948.
Frankel, L. B.; Christoffersen, N. R.; Jacobsen, A.; Lindow, M.; Krogh, A.; Lund, A. H. Programmed Cell Death 4 (PDCD4) Is an Important Functional Target of the MicroRNA MiR-21 in Breast Cancer Cells. J. Biol Chem. 2008, 283, 1026-1033.
Garzon, R.; Colin, G. A.; Croce, C. M. MicroRNAs in Cancer. Annu. Rev. Med. 2009, 60, 167-179.
Geary, C.; Rothemund, P. W.; Andersen, E. S. A Single-Stranded Architecture for Cotranscriptional Folding of RNA Nanostructures. Science 2014, 345, 799-804.

Griffiths-Jones et al. (2006) Nucl. Acids Res. 34:D140-D144.
Griveau, A.; Bejaud, J.; Anthiya, S.; Avril, S.; Autret, D.; Garcion, E. Silencing of MiR-21 by Locked Nucleic Acid-Lipid Nanocapsule Complexes Sensitize Human Glioblastoma Cells to Radiation-Induced Cell Death. Int. J Pharm. 2013, 454, 765-774.
Grodzinski, P.; Farrell, D. Future Opportunities in Cancer Nanotechnology—NCI Strategic Workshop Report. Cancer Res. 2014, 74, 1307-1310.
Grodzinski, P.; Torchilin, V.; (Editors) Adv. Drug Delivery Rev.: Cancer Nanotechnology; vol. 66 ed.; Elsevier: 2014.
Guo, P. The Emerging Field of RNA Nanotechnology. Nat. Nanotechnol. 2010, 5, 833-842.
Guo, P.; Erickson, S.; Anderson, D. A Small Viral RNA Is Required for in vitro Packaging of Bacteriophage Phi29 DNA. Science 1987, 236, 690-694.
Guo, P.; Hague, F.; Hallahan, B.; Reif, R.; Li, H. Uniqueness, Advantages, Challenges, Solutions, and Perspectives in Therapeutics Applying RNA Nanotechnology. Nucleic Acid Ther. 2012, 22, 226-245.
Guo, P.; Zhang, C.; Chen, C.; Trottier, M.; Garver, K. Inter-RNA Interaction of Phage Phi29 PRNA to Form a Hexameric Complex for Viral DNA Transportation. Mol. Cell. 1998, 2, 149-155.
Han, D.; Park, Y.; Kim, H.; Lee, J. B. Self-Assembly of Free-Standing RNA Membranes. Nat. Commun. 2014, 5.
Haque, F.; Shu, D.; Shu, Y.; Shlyakhtenko, L.; Rychahou, P.; Evers, M.; Guo, P. Ultrastable Synergistic Tetravalent RNA Nanoparticles for Targeting to Cancers. Nano Today 2012, 7, 245-257.
Hatakeyama, H.; Murata, M.; Sato, Y.; Takahashi, M.; Minakawa, N.; Matsuda, A.; Harashima, H. The Systemic Administration of an Anti-MiRNA Oligonucleotide Encapsulated PH-Sensitive Liposome Results in Reduced Level of Hepatic MicroRNA-122 in Mice. J Control Release 2013.
Henry, J.; Azevedo-Pouly, A.; Schmittgen, T. MicroRNA Replacement Therapy for Cancer. Pharm Res 2011, 28, 3030-3042.
Hunter, M. P.; Ismail, N.; Zhang, X.; Aguda, B. D.; Lee, E J.; Yu, L.; Xiao, T.; Schafer, J.; Lee, M. L. T.; Schmittgen, T. D.; et al. Detection of MicroRNA Expression in Human Peripheral Blood Microvesicles. PLoS One 2008, 3, e3694.
Hynes, N. E.; Lane, H. A. ERBB Receptors and Cancer the Complexity of Targeted Inhibitors. Nat. Rev. Cancer 2005, 5, 341-354.
Iorio, M. V.; Ferracin, M.; Liu, C. G.; Veronese, A.; Spizzo, R.; Sabbioni, S.; Magri, E.; Pedriali, M.; Fabbri, M.; Campiglio, M.; et. al. MicroRNA Gene Expression Deregulation in Human Breast Cancer. Cancer Res 2005, 65, 7065-7070.
Jasinski, D.; Khisamutdinov, E. F.; Lyubchenko, Y. L.; Guo, P. Physicochemically Tunable Poly-Functionalized RNA Square Architecture With Fluorogenic and Ribozymatic Properties. ACS Nano 2014, 8, 7620-7629.
Kasinski, A. L.; Slack, F. J. Epigenetics and Genetics. MicroRNAs En Route to the Clinic: Progress in Validating and Targeting MicroRNAs for Cancer Therapy. Nat. Rev. Cancer 2011, 11, 849-864.
Khisamutdinov, E. F.; Jasinski, D. L.; Guo, P. RNA as a Boiling-Resistant Anionic Polymer Material to Build Robust Structures With Defined Shape and Stoichiometry. ACS Nano. 2014, 8, 4771-4781.
Khisamutdinov, E.; Li, H.; Jasinski, D.; Chen, J.; Fu, J.; Guo, P. Enhancing Immunomodulation on Innate Immunity by Shape Transition Among RNA Triangle, Square, and Pentagon Nanovehicles. Nucelic Acids Research 2014, 42, 9996-10004.
Kim, J. H.; Yearn, J. H.; Ko, J. J.; Han, M. S.; Lee, K.; Na, S. Y.; Bae, J. Effective Delivery of Anti-MiRNA DNA Oligonudeotides by Functionalized Gold Nanoparticles. J Biotechnol. 2011, 155, 287-292.

\* cited by examiner

SEQUENCE LISTING

```
<160> NUMBER OF SEQ ID NOS: 23

<210> SEQ ID NO 1
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1
uugccaugug uauguggg                                                          18

<210> SEQ ID NO 2
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2
cccacauacu uuguugaucc                                                        20

<210> SEQ ID NO 3
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 3
ggaucaauca uggcaa                                                            16

<210> SEQ ID NO 4
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 4
ggaucaauca uggcaa                                                            16

<210> SEQ ID NO 5
<211> LENGTH: 43
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 5
uugccaugug uaugugggau cccgcggcca uggcggccgg gag                              43

<210> SEQ ID NO 6
<211> LENGTH: 59
<212> TYPE: RNA
<213> ORGANISM: Artificial Sequence
<220> FEATURE:
<223> OTHER INFORMATION: Description of Artificial Sequence: Synthetic
      oligonucleotide
```

```
<400> SEQUENCE: 6
cccacauacu uguugaucc gccuuaguaa cgugcuuuga ugucgauucg acaggaggc        59

<210> SEQ ID NO 7
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
gataagctct cccggccgcc atggccgcgg gat                                  33

<210> SEQ ID NO 8
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
ctcccggccg ccatggccgc gggat                                           25

<210> SEQ ID NO 9
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 9
aucccgcggc cauggcggcc gggag                                           25

<210> SEQ ID NO 10
<211> LENGTH: 39
<212> TYPE: RNA
<213> ORGANISM: Unknown
<220> FEATURE:
<223> OTHER INFORMATION: Description of Unknown:
      Aptamer sequence

<400> SEQUENCE: 10
gccuuaguaa cgugcuuuga ugucgauucg acaggaggc                            39

<210> SEQ ID NO 11
<211> LENGTH: 8
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11 gataagct                                                               8

<210> SEQ ID NO 12
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 12
```
ucuuugguua ucuagcugua ug                                                22

<210> SEQ ID NO 13
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 13
uacccuguag aaccgaauuu gug                                               23

<210> SEQ ID NO 14
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 14
uucaaguaau ccaggauagg cu                                                22

<210> SEQ ID NO 15
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 15
ugagguagua gguuguauag uu                                                22

<210> SEQ ID NO 16
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 16
aggcggagac uugggcaauu g                                                 21

<210> SEQ ID NO 17
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 17
uggcaguguc uuagcugguu gu                                                22

<210> SEQ ID NO 18
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 18

```
cguuucaca gcggaccuug au                                              22

<210> SEQ ID NO 19
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 19
guccaguuuu cccaggaauc ccu                                            23

<210> SEQ ID NO 20
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 20
aacauucauu gcugucggug ggu                                            23

<210> SEQ ID NO 21
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
agcactttct cccggccgcc atggccgcgg gat                                 33

<210> SEQ ID NO 22
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
atttgcacct cccggccgcc atggccgcgg gat                                 33

<210> SEQ ID NO 23
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Asp Glu Val Asp
1
```

MIRNA FOR TREATMENT OF BREAST CANCER

RELATED APPLICATIONS

The application is a § 371 National State Application of PCT/US2016/021451 filed Mar. 9, 2016 which claims the benefit of U.S. Provisional Patent Application No. 62/130,533, filed Mar. 9, 2015, and 62/175,774, filed Jun. 15, 2015, the entire disclosures of which are hereby incorporated by reference in their entirety.

GOVERNMENT INTEREST

This invention was made with government support under EB019036, CA 151648 and EB0037305 awarded by the National Institutes of Health, and under BC 140428 awarded by the Department of Defense. The government has certain rights in the invention.

SEQUENCE LISTING

The instant application contains a Sequence Listing which has been filed electronically in ASCII format and is hereby incorporated by reference in its entirety. Said ASCII copy, created on Jul. 9, 2019, is named 2935720-9_SL.txt and is 5,679 bytes in size.

TECHNICAL FIELD

The presently-disclosed subject matter relates to RNA nanostructure and method to treat breast cancer in a subject. More particularly, the presently disclosed subject matter relates to a RNA nanostructure and composition containing a multiple branched RNA nanoparticle, a breast cancer targeting module, and an effective amount of a breast cancer therapeutic agent. Further, the presently disclosed subject matter relates to a method of using the RNA nanoparticle composition to treat breast cancer in a subject having or at risk of having breast cancer.

INTRODUCTION

Triple negative breast cancers (TNBCs) have high mortality owing to aggressive proliferation and metastasis and a lack of diversified treatment options. TNBCs, which represent IS to 20 percent of breast cancers, occur more frequently in young women. African American women, and individuals carrying the BRCA1 gene. Currently, there is no curative treatment for TNBC, and the available chemotherapy is associated with significant toxicity and development of drug resistance. As a result, the prognosis for TNBC patients remains poor. The five-year survival rate is less than 74.5% in comparison with 87% for HER2 positive breast cancer and over 90% for ER positive breast cancer. Thus, there is an urgent and unmet need for the development of TNBC targeted therapeutics. This introduction is only provided for general background information and is not intended to be used as an aid in determining the scope of the claimed subject matter.

SUMMARY

The presently-disclosed subject matter meets some or all of the above-identified needs, as will become evident to those of ordinary skill in the art after a study of information provided in this document.

This Summary describes several embodiments of the presently-disclosed subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently-disclosed subject matter, whether listed in this Summary or not. This Summary does not list or suggest all possible combinations of such features.

The presently-disclosed subject matter relates to RNA-based composition and method to treat breast cancer in a subject. More particularly, the presently disclosed subject matter relates to a RNA nanostructure and composition containing a multiple branched RNA nanoparticle, a breast cancer targeting module, and an effective amount of a breast cancer therapeutic agent. Further, the presently disclosed subject matter relates to a method of using the RNA nanoparticle composition to treat breast cancer in a subject having or at risk of having breast cancer.

The presently disclosed subject matter relates to an artificial RNA nanostructure molecule. The molecule includes a multiple branched RNA junction motif comprising at least one RNA oligonucleotides, and a breast cancer targeting module coupled to the RNA junction motif. In some embodiments, the molecule further includes at least one bioactive agent coupled to the RNA junction motif. In some embodiments, the RNA oligonucleotides is at least 3 nucleotides in length. In some embodiments, the bioactive agent is a therapeutic agent. In some embodiments, the RNA oligonucleotide includes at least one chemical modification at the 2' position. Non-limiting examples of the chemical modification includes 2'Fluoro, 2'Amine, and 2'O-Methyl. In some embodiments, the multiple branched RNA junction motif is a three-branched RNA junction motif. In some embodiments of the present disclosure, the RNA molecules form dimers, trimers, hexamers, and patterned superstructures. Further, In some embodiments, the multiple branched RNA comprises sequence 5'-UUG CCA UGU GUA UGU GGG AUC CCG CGG CCA UGG CGG CCG GGA G-3' (SEQ ID NO: 5). In some embodiments, the multiple branched RNA comprises sequence 5'-CCC ACA UAC UUU GUU GAU CCG CCU UAG UAA CGU GCU UUG AUG UCG AUU CGA CAG GAG GC-3'(SEQ ID NO: 6). In some embodiments, the multiple branched RNA comprises sequence 5'-GA-TAAGCT CTC CCG GCC GCC ATG GCC GCG GGA T-3' (SEQ ID NO: 7). In some embodiments, the multiple branched RNA comprises a sequence 5'-CTC CCG GCC GCC ATG GCC GCG GGA T-3' (SEQ ID NO: 8). In some embodiments, the multiple branched RNA comprises a sequence 5'-AUC CCG CGG CCA UGG CGG CCG GGA G-3' (SEQ ID NO: 9). In some embodiments, the diameter of the molecule is at least about 40 nm or less. In some embodiments, the diameter of the molecule is at least about 20 nm or less. In some embodiments, the diameter of the molecule is at least about 10 nm or less. In some embodiments, the molecule has zeta potential ranging from about −100 mV to about 100 mV. In some embodiments, the molecule has zeta potential ranging from about −50 my to about 50 mV. In some embodiments, a branch of the three-branched RNA junction motif includes an a3WJ RNA module (SEQ ID NO: 1), a b3WJ RNA module (SEQ ID NO: 2), or a c3WJ RNA module (SEQ ID NO: 3). In some embodiments, the three-branched RNA junction motif comprises an a3WJ RNA module (SEQ ID NO: 1); a b3WJ RNA module (SEQ ID NO: 2); and a c3WJ RNA module (SEQ ID NO: 3). In some embodiments, SEQ ID NO: 1 comprises nucleotide sequence 5'-UUG CCA UGU GUA UGU GGG-3'. In some embodiments, SEQ ID NO: 2 comprises nucleotide sequence 5'-CCC ACA UAC UUU GUU GAUCC-3'. In some embodiments, SEQ ID NO: 3 comprises nucleotide sequence 5'-GGA UCA AUC AUG GCA A-3'.

In some embodiments, the breast cancer targeting module includes a ligand that binds to at least one breast cancer cell surface marker. In some embodiments, the ligand binds to a folate receptor, an epidermal growth factor receptor 2 (ErbB-2/HER2), an epidermal growth factor receptor (EGFR), a HER2, or a combination thereof. In some embodiments, the ligand is an aptamer. In some embodiments, the ligand is a EGFR targeting aptamer. In some embodiments, the aptamer binds to EGFR, PDGFR, folate receptor, or a combination thereof. In some embodiments, the aptamer has sequence 5'-G CCU UAG UAA CGU GCU UUG AUG UCG AUU CGA CAG GAG GC-3'(SEQ ID NO: 10). In some embodiments, targeting module is a folate. Non-limiting examples of the folate are folic acid, 5-methyltetrahydro folate, 5-formyltetrahydrofolate, dihydrofolate, tetrahydrofolate, or other folate compounds.

In some embodiments, the presently disclosed subject matter provides that the bioactive agent is a therapeutic agent. In some embodiments, the bioactive agent is a drug, a fluorescent dye, or a chemical, or a combination thereof. In some embodiments, the bioactive agent is a siRNA, a miRNA, an anti-miRNA, a ribozyme RNAs, an antisense RNAs. In some embodiments, the bioactive agent is directed to a breast cancer marker. In some embodiments, the bioactive agent is a siRNA sequence or a microRNA sequence. In some embodiments, the siRNA binds to a mRNA molecule of an oncogene. Non-limiting oncogene includes RAS, cMET, HER2, MDM2, PIK3CA, AKT, CDK4, or a combination thereof.

In some embodiments, the bioactive agent is an anti-miRNA molecule for a miRNA to interfere with miRNA to regress cancer growth. Non-limiting example of miRNA includes miR-9, miR-10b, miR-21, miR-17, and miR-26. In some embodiments, the RNA nanostructure molecule introduces tumor suppressive miRNAs to rescue down-regulated tumor suppressive miRNAs. Non-limiting examples of the miRNA include let-7a, miR-10b, miR-25, miR-34a, miR-124, miR-145, and miR-181b. In some embodiments, the microRNA sequence is an anti-miR-21 sequence.

In some embodiments, non-limiting examples of the miRNA sequence comprises 5'-GATAAGCT-3' (SEQ ID NO: 11), 5'-AGCACTTT-3', or 5'-ATTTGCAC-3'. In some embodiments, the miRNA is a LNA miRNA sequence. Non-limiting examples of the LNA miRNA sequences are 5'-+G+A+T+A+A+G+C+T-3' (SEQ ID NO: 11), 5'-+A+G+C+A+C+T+T+T-3', or 5'-+A+T+T+T+G+C+A+C-3'. In some embodiments, the RNA nanostructure inhibit breast cancer cells proliferation.

Further provided in some embodiments, is a nucleic acid composition that includes a therapeutically effective amount of the RNA nanostructure molecule as disclosed above and herein. In some embodiments, the composition further includes a pharmaceutically acceptable carrier.

Still further, in some embodiments, the presently disclosed subject matter provides a nanoparticle delivery system, comprising a RNA nanostructure molecule as disclosed above and herein. In some embodiments, the nanoparticle delivery system further includes a pharmaceutically acceptable carrier.

In some embodiments, the presently disclosed subject matter further provides a method of treating a brain tumor in a subject having or at risk of developing a breast cancer The method comprising administering to the subject a therapeutically effective amount of a composition comprising a RNA nanostructure molecule as disclosed above and herein. In some embodiments, the composition further comprises a pharmaceutically acceptable carrier. In some embodiments, the subject is a mammal or a non-mammal vertebrate. In some embodiments, the subject is a human. In some embodiments, the breast cancer is triple negative breast cancer.

BRIEF DESCRIPTION OF THE DRAWINGS

The features of the presently disclosed subject matter are set forth with particularity in the appended claims. A better understanding of the features and advantages of the presently disclosed subject matter will be obtained by reference to the following detailed description that sets forth illustrative embodiments, in which the principles of the subject matter are used, and the accompanying drawings of which. The drawings were originally published in color, incorporated by reference in their entireties (Dan Shu, et al., (2015) ACS Nano, Vol. 9, No. 10, 9731-9740). The black and white drawings of the instant application correspond to the color ones published.

FIG. 1A is a diagram illustrating sequence of phi29 pRNA-3WJ core. FIG. 1A discloses the "$a_{3WJ}$" sequence as SEQ ID NO: 1, the "$b_{3WJ}$" sequence as SEQ ID NO: 2 and the "$c_{3WJ}$" sequence as SEQ ID NO: 3. FIG. 1B is s a diagram showing the 3D model of arm-extended RNA nanoparticles using 3WJ as scaffold. FIG. 1C is an image showing atomic force microscopy (AFM) image of the nanoparticle in FIG. 1B. FIG. 1D is a graph showing the size of the 3WJ core determined by dynamic light scattering (DLS). FIG. 1E is a graph showing the zeta potential of the 3WJ core.

FIG. 2A is a diagram showing the 2D sequence of the nanoparticle harboring three functional modules: EGFR RNA aptamer for targeted delivery, anti-miR-21 LNA for therapy, and Alexa-647 dye for imaging. FIG. 2A discloses the "Strand 1" sequence as SEQ ID NO: 4, the "Strand 2" sequence as SEQ ID NO: 5, the "Strand 3" sequence as SEQ ID NO: 6 and the "Strand 4" sequence as SEQ ID NO: 7. FIG. 2B is an image showing the native PAGE showing stepwise highly efficient assembly of the RNA nanoparticle. FIG. 2C is a graph illustrating the DLS measurements showing the hydrodynamic size. FIG. 2D is a graph illustrating the Zeta potential. FIG. 2E is a graph showing the serum stability assay. FIG. 2F is a graph showing the apparent $T_m$ extracted from temperature gradient gel electrophoresis (TGGE, insert).

FIG. 3A is a confocal images showing efficient binding and internalization into MDA-MB-231 cells. Green: cytoplasm; blue: nuclei; and red: RNA nanoparticle. FIG. 3B is a graph showing flow cytometry) assay showing the binding to MDA-MB-231 cells. FIG. 3C is a graph illustrating Dual-luciferase assay demonstrating in vitro delivery of anti-miR-21 LNA into MDA-MB-231 cells. FIG. 3D is a graph showing qRT-PCR assay depicting the effect of miR-21 knockdown on target gene expression level of PTEN and PDCD4 after treatment. RQ: relative quantification. FIG. 3E is a graph showing caspase-3 assay showing the cellular apoptotic effects of MDA-MB-231 cells after treatment.

FIG. 4A is an image showing the tumor inhibition over the course of 5 injections. The endpoint luminescence indicates the tumor volume. FIG. 4B is a graph showing tumor growth curve over the course of 5 injections. ($*P<0.05$, $**P<0.01$, error bars indicate SEM). FIG. 4C includes fluorescence images showing specific targeting and retention in TNBC tumors 8 hrs post-injection. FIG. 4D includes images showing histological assay of breast tumor frozen cross-sections (10 μm thick) by fluorescence confocal microscopy showing binding and internalization. Blue: nuclei; red: RNA nanoparticle. FIG. 4E includes graphs showing real-time PCR at the mRNA level and FIG. 4F includes images showing western blot at the protein level showing the down-regulation of miR-21 after treatment, resulting in up-regulation of two target genes PTEN and PDCD4. Lamin A/C was internal control. RQ: relative quantification.

DESCRIPTION OF EXEMPLARY EMBODIMENTS

Figure 1:
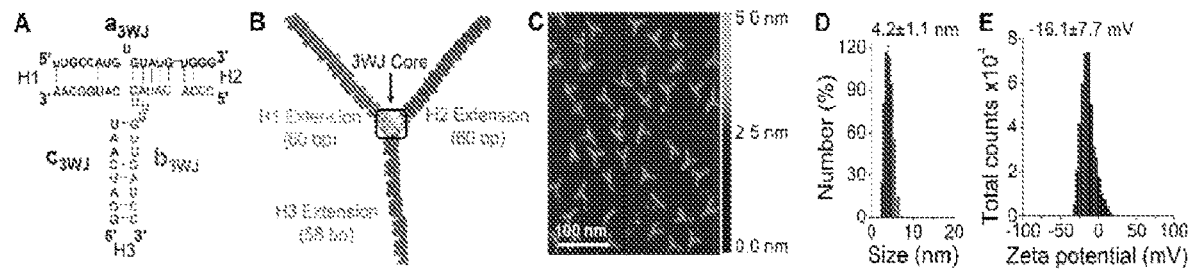
FIGS. 1A-1E are graphs and diagrams illustrating characterization and introduction of the system for pRNA-3WJ nanoparticle construction.

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In certain instances, nucleotides and polypeptides disclosed herein are included in publicly-available databases, such as GENBANK® and SWISSPROT. Information including sequences and other information related to such nucleotides and polypeptides included in such publicly-available databases are expressly incorporated by reference. Unless otherwise indicated or apparent the references to such publicly-available databases are references to the most recent version of the database as of the filing date of this Application.

While the terms used herein are believed to be well understood by one of ordinary skill in the art, definitions are set forth to facilitate explanation of the presently-disclosed subject matter.

Unless defined otherwise, all technical and scientific terms used herein have the same meaning as commonly understood by one of ordinary skill in the art to which the presently-disclosed subject matter belongs. Although any methods, devices, and materials similar or equivalent to those described herein can be used in the practice or testing of the presently-disclosed subject matter, representative methods, devices, and materials are now described.

Following long-standing patent law convention, the terms "a", "an", and "the" refer to "one or more" when used in this application, including the claims. Thus, for example, reference to "a cell" includes a plurality of such cells, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method. As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

The presently disclosed subject matter relates to an artificial RNA nanostructure molecule. The molecule includes a multiple branched RNA junction motif comprising at least one RNA oligonucleotides, and a breast cancer targeting module coupled to the RNA junction motif. In some embodiments, the molecule further includes at least one bioactive agent coupled to the RNA junction motif. In some embodiments, the RNA oligonucleotides is at least 6 nucleotides in length. In some embodiments, the bioactive agent is a therapeutic agent. In some embodiments, the RNA oligonucleotide includes at least one chemical modification at the 2' position. Non-limiting examples of the chemical modification includes 2' Fluoro, 2' Amine, and 2'O-Methyl.

The term "RNA" refers to a molecule comprising at least one ribonucleotide residue. By "ribonucleotide" is meant a nucleotide with a hydroxyl group at the 2' position of a β-D-ribofuranose moiety. The terms encompass double stranded RNA, single stranded RNA, RNAs with both double stranded and single stranded regions, isolated RNA such as partially purified RNA, essentially pure RNA, synthetic RNA, recombinantly produced RNA, as well as altered RNA, or analog RNA, that differs from naturally occurring RNA by the addition, deletion, substitution, and/or alteration of one or more nucleotides. Such alterations can include addition of non-nucleotide material, such as to the end(s) of an siRNA or internally, for example at one or more nucleotides of the RNA. Nucleotides in the RNA molecules of the presently disclosed subject matter can also comprise non-standard nucleotides, such as non-naturally occurring nucleotides or chemically synthesized nucleotides or deoxynucleotides. These altered RNAs can be referred to as analogs or analogs of a naturally occurring RNA.

As described herein, RNA nanotechnology refers to the design, fabrication, and application of nanometer scale RNA architectures constructed via bottom-up self-assembly with its major frame composed mainly of RNA (14, 17-29). RNA nanotechnology has recently emerged as an important field due to recent finding of its high thermodynamic stability, favorable and distinctive in vivo attributes (US 2014/0179758, hereby incorporate by reference in its entirety). In some embodiments of the present disclosure, as disclosed in US2014/0179758, the RNA molecules form dimers, trimers, hexamers, and patterned superstructures. This is distinct from conventional nanomaterials typically used to deliver anti-miRNAs (30), such as lipid (31-33), polymer (34,35), and inorganic nanomaterials (36). For RNA nanotechnology based particles, scaffolds, targeting ligands, therapeutic moieties, and regulators can all be composed of RNA nucleotides. Another important distinction is that RNA nanotechnology focuses on inter-RNA interactions (between molecules) and quaternary (4D) structure, while classical studies on RNA structure and function focuses on intra-RNA interactions (within a molecule) and secondary (2D)/tertiary (3D) structure. Over the years, several challenges have deterred widespread use of RNA as a construction material, such as sensitivity to RNase degradation; susceptibility to dissociation after systemic injection; and, toxicity and adverse immune responses. These challenges have been overcome to a large extent: 2'-fluoro (2'-F) or 2'-O-methyl (2'-OMe) modifications on the —OH group of the ribose can make the RNA chemically stable in the serum (37); certain naturally occurring junction motifs are thermodynamically stable and can keep the entire RNA nanoparticle intact at ultra-low concentrations (38-40); and finally, immunogenicity of RNA nanoparticle is sequence and shape dependent, and is tunable to make RNA nanoparticles stimulate the production of inflammatory cytokines (41), or to make the RNA nanoparticles non-immunogenic and non-toxic even at repeated i.v. administrations of 30 mg/kg (42). It is also expected that RNA nanotechnology will play a critical role in the application of exosome RNA for therapy (43-47).

As disclosed herein, RNA nanoparticles can be fabricated with precise control of shape, size and stoichiometry, as demonstrated by the packaging RNA (pRNA) of the bacteriophage phi29 DNA packaging motor, which forms dimmers, trimers, and hexamers via hand-in-hand interactions of the interlocking loops. In some embodiments, a branch of the three-branched RNA junction motif includes an a3WJ RNA module (SEQ ID NO: 1), a b3WJ RNA module (SEQ ID NO: 2), or a c3WJ RNA module (SEQ ID NO: 3). In some embodiments, the three-branched RNA junction motif comprises an a3WJ RNA module (SEQ ID NO: 1); b3WJ RNA module (SEQ ID NO: 2); and a c3WJ RNA module (SEQ ID NO: 3). In some embodiments, SEQ ID NO: 1 comprises nucleotide sequence 5'-UUG CCA UGU GUA UGU GGG-3'. In some embodiments, SEQ ID NO: 2 comprises nucleotide sequence 5'-CCC ACA UAC UUU GUU GAUCC-3'. In some embodiments, SEQ ID NO: 3 comprises nucleotide sequence 5'-GGA UCA AUC AUG GCA A-3'.

In some embodiments, the multiple branched RNA junction motif is a three-branched RNA junction motif. In some embodiments, the multiple branched RNA comprises sequence 5'-UUG CCA UGU GUA UGU GGG AUC CCG CGG CCA UGG CGG CCG GGA G-3' (SEQ ID NO: 5). In some embodiments, the multiple branched RNA comprises sequence 5'-CCC ACA UAC UUU GUU GAU CCG CCU UAG UAA CGU GCU UUG AUG UCG AUU CGA CAG GAG GC-3'(SEQ ID NO: 6). In some embodiments, the multiple branched RNA comprises sequence 5'-GA-TAAGCT CTC CCG GCC GCC ATG GCC GCG GGA T-3' (SEQ ID NO: 7). In some embodiments, the multiple branched RNA comprises a sequence 5'-CTC CCG GCC GCC ATG GCC GCG GGA T-3' (SEQ ID NO: 8). In some embodiments, the multiple branched RNA comprises a sequence 5'-AUC CCG CGG CCA UGG CGG CCG GGA G-3' (SEQ ID NO: 9).

In some embodiments, the diameter of the molecule is at least about 40 nm or less. The diameter is at least about 35 nm or less, at least about 30 nm or less, at least about 25 nm or less, at least 20 nm or less, at least 15 nm or less, at least 10 nm or less, at least 5 nm or less.

In some embodiments, the molecule has zeta potential ranging from about −150 mV to about 150 mV. The RNA molecule has a zeta potential ranging from about −140 mV to about 140 mV, from about −130 mV to about 130 mV, from about −120 mV to about 120 mV, from about −110 mV to about 110 mV. In some embodiments, the molecule has zeta potential ranging from about −100 mV to about 100 mV. The RNA molecule has a zeta potential ranging from about −95 mV to about 95 mV, from about −90 mV to about 90 mV, from about −85 mV to about 85 mV, from about −80 mV to about 80 mV, from about −75 mV to about 75 mV, from about −70 to about 70 mV, form about −65 mV to about 65 mV, from about −60 mV to about 60 mV, from about −55 mV to about 55 mV, from about −50 mV to about 50 mV. The molecule has a zeta potential ranging from about −45 my to about 45 mV, from about −40 mV to about 40 mV, from about −35 mV to about 35 mV, from about −35 mV to about 30 mV, from about −35 mV to about 20 mV, from about −25 mV to about 15 mV.

In some embodiments, the RNA nanostructure molecule is substantially stable in pH ranges from about 2 to about 13. The RNA molecule is substantially stable in pH about 2, 3, 4, 5, 6, 7, 8, 9, 10, 11, 12 and 13. As used herein, the term "substantially stable" can refer to physical and/or chemical stability. As will be recognized by those of ordinary skill in the art, the term "substantially stable" can refer to stability of the composition under certain conditions, relative to an initial composition (i.e., when a particular batch of the composition is initially prepared). In this regard, as will be recognized by those of ordinary skill in the art, one manner in which stability of a particular embodiment of the composition can be determined is as follows: preparing a batch of the embodiment of the composition, making an initial assessment of a sample of the composition (control sample), subjecting a sample of the composition to conditions of interest (e.g., storage at a particular condition for a particular time period) (test sample), making an assessment of the test sample, and comparing the assessment of the control sample to the assessment of the test sample. Calculations can be made to determine whether the amounts present in the test sample are 100%±20, 19, 18, 17, 16, 15, 14, 13, 12, 11, 10, 9, 8, 7, 6, 5, 4, 3, 2, 1, 0.5, or 0.1% of the amount that is in the control sample.

In some embodiments, the breast cancer targeting module includes a ligand that binds to at least one breast cancer cell surface marker. In some embodiments, the ligand binds to a folate receptor, an epidermal growth factor receptor 2 (ErbB-2/HER2), an epidermal growth factor receptor (EGFR), a HER2, or a combination thereof. In some embodiments, the ligand is an aptamer. The term "aptamer" as used herein refers to an oligonucleotide that can bind specifically to its target with high affinity. In some embodiments, the ligand is a EGFR targeting aptamer. In some embodiments, the aptamer has sequence 5'-G CCU UAG UAA CGU GCU UUG AUG UCG AUU CGA CAG GAG GC-3'(SEQ ID NO: 10). In some embodiments, targeting module is a folate.

The term "folate" as used herein can comprise a genus of well-defined B-vitamin compounds, including but not limited to, 5-methyltetrahydro folate, 5-formyltetrahydrofolate, dihydrofolate, tetrahydrofolate, folic acid and other folate compounds. Since folate is an essential component required during DNA replication and methylation in highly proliferating cells, many cancer cells, such as those of the brain, ovary, lung, breast, kidney, endometrium, colon and bone marrow, over-express FRs to increase folate uptake.

In some embodiments, the presently disclosed subject matter provides that the bioactive agent is a therapeutic agent. In some embodiments, the bioactive agent is a drug, a fluorescent dye, or a chemical, or a combination thereof. In some embodiments, the bioactive agent includes an imaging module. Non-limiting examples of the imaging module is fluorescent dye, including a non-limiting example Alexa647. In some embodiments, the bioactive agent is a siRNA, a miRNA, an anti-miRNA, a ribozyme RNAs, an antisense RNAs. In some embodiments, the bioactive agent is directed to a breast cancer marker. In some embodiments, the bioactive agent is a siRNA sequence or a microRNA sequence. In some embodiments, the microRNA sequence is an anti-miR-21 sequence. In some embodiments, the anti-miR-21 sequence comprises 5'-GATAAGCT-3' (SEQ ID NO: 11). In some embodiments, the RNA nanostructure inhibit breast cancer cells proliferation.

The terms "small interfering RNA", "short interfering RNA", "small hairpin RNA", "siRNA", and shRNA are used interchangeably and refer to any nucleic acid molecule capable of mediating RNA interference (RNAi) or gene silencing. See e.g., Bass, Nature 411:428-429, 2001; Elbashir et al., Nature 411:494-498, 2001a; and PCT International Publication Nos. WO 00/44895, WO 01/36646, WO 99/32619, WO 00/01846, WO 01/29058, WO 99/07409, and WO 00/44914. In one embodiment, the siRNA comprises a double stranded polynucleotide molecule comprising complementary sense and antisense regions, wherein the antisense region comprises a sequence complementary to a region of a target nucleic acid molecule (for example, a nucleic acid molecule encoding BRCAA1). In another embodiment, the siRNA comprises a single stranded polynucleotide having self-complementary sense and antisense regions, wherein the antisense region comprises a sequence complementary to a region of a target nucleic acid molecule. In another embodiment, the siRNA comprises a single stranded polynucleotide having one or more loop structures and a stem comprising self complementary sense and antisense regions, wherein the antisense region comprises a sequence complementary to a region of a target nucleic acid molecule, and wherein the polynucleotide can be processed either in vivo or in vitro to generate an active siRNA capable of mediating RNAi. As used herein, siRNA molecules need not be limited to those molecules containing only RNA, but further encompass chemically modified nucleotides and non-nucleotides.

In some embodiments, the presently disclosed subject matter takes advantage of the ability of short, double stranded RNA molecules to cause the down regulation of cellular genes, a process referred to as RNA interference. As used herein, "RNA interference" (RNAi) refers to a process of sequence-specific post-transcriptional gene silencing mediated by a small interfering RNA (siRNA). See Fire et al., Nature 391:806-811, 1998 and U.S. Pat. No. 6,506,559, each of which is incorporated by reference herein in its entirety. The process of post-transcriptional gene silencing is thought to be an evolutionarily conserved cellular defense mechanism that has evolved to prevent the expression of foreign genes (Fire, Trends Genet 15:358-363, 1999).

In some embodiments, the term "MicroRNAs (miRNAs)" as used herein are single-stranded, or double stranded non-coding RNAs, at least about 6 nucleotide in length that can regulate gene expression at the post-transcriptional level by either degrading their target mRNAs or inhibiting their translation (1,2). MiRNAs play important roles in regulating cell cycle, proliferation, differentiation, metabolism, and apoptosis (1). A compendium of microRNA and respective microRNA binding sequences is available at the miRNA registry. (See, e.g., Griffiths-Jones et al. (2006) Nucl. Acids Res. 34:D140-D144; US20140045709, herein incorporate by reference in their entireties.) In particular embodiments, the microRNA and microRNA binding sequence employed in the present assay are associated with a disease or condition, wherein an antagonist or agonist to the microRNA would be useful in preventing or treating the disease or condition. Dysregulation of miRNAs has been implicated in tumor initiation, progression, and metastasis in several cancer types (3-8). MiRNAs hold great potentials for cancer therapy particularly because one miRNA can regulate a broad set of target genes efficiently and simultaneously, and can therefore address the heterogeneous nature of cancer. Naturally occurring miRNA further displays reduced immune response and low toxicity. Both anti-miRNAs to knockdown oncogenic miRNAs and mimics of miRNAs to upregulate endogenous miRNAs have been developed as therapeutic strategies to achieve tumor regression (6,9,10). However, the major limiting factor is the ability to specifically deliver these therapeutic modules to affected cells and tissues. Nanotechnology holds great promise in this regard and several nanoplatforms have been pursued, but effective strategies to inhibit tumor progression are still lacking (11). Major challenges from formulation and delivery perspective include particle heterogeneity, particle aggregation, particle dissociation, unfavorable pharmacokinetics (PK) and pharmacodynamics (PD) profiles, undesirable toxicity and immunogenicity, and difficulty to overcome biological barriers surrounding tumors (11,12). In addition, unstable thermodynamic properties and lack of controlled release mechanisms have slowed their clinical translation (13). Controlled "active" targeting is desirable to effectively block cancer progression and prevent metastases, while minimizing adverse side effects (13). Liver and other organ accumulations lead to low cancer targeting and high side-effect or toxicity. In the present disclosure, an RNA nanotechnology approach is used to overcome some of the aforementioned challenges in cancer nanotechnology and deliver anti-miRNAs to inhibit tumor growth, using triple negative breast cancer (TNBC) as a model system. To date, there are no targeted therapies available for TNBC, an aggressive breast cancer subtype defined by the lack of estrogen receptor, progesterone receptor, and human epidermal growth factor receptor 2 expression (15). TNBC patients are poorly responsive to chemotherapy, and are susceptible to relapse and early metastatic spread, which leads to poor prognosis and short survival (16).

In some embodiments, the present disclosure provides inhibitors of miRNAs (e.g., anti-miR-21). Compositions comprising such inhibitors and methods for inhibiting miR-21 using such inhibitors are also disclosed herein. Any miRNA inhibitor may be used alone, or with other miRNA inhibitor(s) known in the art. In some embodiments, the miRNA inhibitor comprises an antisense molecule. In some embodiments, the antisense molecule could be a single or a double stranded sequence. Examples of antisense molecule include, but are not limited to, siRNAs, triple-helix-forming agents, ribozymes, RNAi, synthetic peptide nucleic acids (PNAs), antigenes (agRNAs), LNA/DNA copolymers, small molecule chemical compounds, and antisense oligonucleotides.

In some embodiments, the microRNA sequence is at least 6 nucleotide in length. In some embodiments, the miRNA molecule or an equivalent, or a mimic thereof is from about 3 to about 30 nucleotides in length. In some embodiments, the miRNA is about 12 to about 30 nucleotides in length. In some embodiments, the miRNA is from about 15 to about 28 nucleotides in length. In some embodiments, the miRNA is about 19 to about 25 nucleotides in length. In some embodiments, the miRNA has a length of at least about 3, 4, 5, 6, 7, 8, 9, 10, 11, 12, 13, 14, 15, 16, 17, 18, 19, 20, 21, 22, 23, 24, 25, 26, 27, 28, 29, and about 30 nucleotides or more. In some embodiments, an antagomir of a miRNA molecule is from about 6 to about 30 nucleotides in length, from about 10 to about 30 nucleotides in length, from about 12 to about 28 nucleotides in length. In some embodiments, the antagomir of a miRNA molecule has a length of at least about 3, 4, 5, 6, 7, 8, 9, 10, 11, 12, 13, 14, 15, 16, 17, 18, 19, 20, 21, 22, 23, 24, 25, 26, 27, 28, 29, 30 nucleotides or more.

In some embodiments, the miRNA interferes oncogenic miRNA to regress cancer growth. The RNA nanostructure molecule contains anti-miRNA that silences oncogenic miRNAs, including but not limited to, miR-9, miR-10b, miR-21, miR-17, and miR-26. In some embodiments, the miRNA rescues down-regulated cancer suppressive miRNAs, where the RNA nanostructure introduces cancer suppressive miRNAs, including but not limited to, let-7a, miR-10b, miR-25, miR-34a, miR-124, miR-145, and miR-181b. Further examples is disclosed in US20140045709, which herein incorporate by reference in its entirety. Exemplary miRNA sequences are listed below:

```
miR-9:
                              (SEQ ID NO: 12)
5'-UCUUUGGUUA UCUAGCUGUA UG-3' miR-10b:
                              (SEQ ID NO: 13)
5'-UACCCUGUAGAACCGAAUUUGUG-3' miR-26a:
                              (SEQ ID NO: 14)
5'-UUCAAGUAAUCCAGGAUAGGCU-3' let-7a:
                              (SEQ ID NO: 15)
5'-UGAGGUAGUAGGUUGUAUAGUU-3' miR-25:
                              (SEQ ID NO: 16)
5'-AGGCGGAGACUUGGGCAAUUG-3' miR-34a:
                              (SEQ ID NO: 17)
5'-UGGCAGUGUCUUAGCUGGUUGU-3' miR-124:
                              (SEQ ID NO: 18)
5'-CGUGUUCACAGCGGACCUUGAU-3' miR-145:
                              (SEQ ID NO: 19)
5'-GUCCAGUUUUCCCAGGAAUCCCU-3' miR-181b:
                              (SEQ ID NO: 20)
5'-AACAUUCAUUGCUGUCGGUGGGU-3'
```

In some embodiments, the microRNA includes a locked nucleic acid (LNA) sequence. In some embodiments, the microRNA is a

```
LNA-anti-miR21 sequence
                              (SEQ ID NO: 7)
5'-+G + A + T + A + A + G + C + T CTC CCG GCC GCC
ATG GCC GCG GGA T-3' (underlined sequence is 8-mer
anti-miR21 LNA, and "+" denotes LNA sequence).
```

In some embodiments, the RNA nanostructure contains a strand LNA17_sphl: 5'-+A+G+C+A+C+T+T+TCTCCCGGCCGCCATGGCCGCGGGAT-3' (SEQ ID NO: 21) ("+" denotes LNA sequence.) In another embodiment, the RNA nanostructure contains a strand of LNA19a_sphl: 5'-+A+T+T+T+G+C+A+CCTCCCGGCC-GCCATGGCCGCGGGAT-3' (SEQ ID NO: 22) ("+" denotes LNA sequence).

The phrase "breast cancer marker" as used herein refers to genes or gene products (e.g., RNA molecules or proteins) which are characteristic of some or all of the cells in breast cancer. A breast cancer marker with diagnostic value can be a gene or gene product expressed in normal, non-cancerous cells, but is characteristic of a type or classification of cancer by, for example, its over-expression or under-expression as compared to its expression in normal, non-cancerous cells. A breast tumor marker with prognostic value is a gene or gene product for which the over-expression or under-expression confers predictive information about the future aggressiveness of a cancer and/or its response to therapy at the time of diagnosis. In a cancer sample, the patterns of expression of diagnostic and prognostic cancer markers allow one to accurately identify and determine the future course of the disease, respectively. Non-limiting examples of breast cancer biomarkers are described in WO2010017515 (herein incorporated by reference in its entirety).

In another aspect of the present disclosure, in some embodiments, is a nucleic acid composition that includes a therapeutically effective amount of the RNA nanostructure molecule as disclosed above and herein. In some embodiments, the composition further includes a pharmaceutically acceptable carrier.

Further, in some embodiments, the presently disclosed subject matter provides a nanoparticle delivery system, comprising a RNA nanostructure molecule as disclosed above and herein. In some embodiments, the nanoparticle delivery system further includes a pharmaceutically acceptable carrier.

The term "pharmaceutically acceptable carrier" as used herein refers to a diluent, adjuvant, excipient, or vehicle with which a heterodimeric probe of the disclosure is administered and which is approved by a regulatory agency of the federal or a state government or listed in the U.S. Pharmacopeia or other generally recognized pharmacopeia for use in animals, and more particularly in humans. Such pharmaceutical carriers can be liquids, such as water and oils, including those of petroleum, animal, vegetable, or synthetic origin, such as peanut oil, soybean oil, mineral oil, sesame oil, and the like. The pharmaceutical carriers can be saline, gum acacia, gelatin, starch paste, talc, keratin, colloidal silica, urea, and the like. When administered to a patient, the heterodimeric probe and pharmaceutically acceptable carriers can be sterile. Water is a useful carrier when the heterodimeric probe is administered intravenously. Saline solutions and aqueous dextrose and glycerol solutions can also be employed as liquid carriers, particularly for injectable solutions. Suitable pharmaceutical carriers also include excipients such as glucose, lactose, sucrose, glycerol monostearate, sodium chloride, glycerol, propylene, glycol, water, ethanol, and the like. The present compositions, if desired, can also contain minor amounts of wetting or emulsifying agents, or pH buffering agents. The present compositions advantageously may take the form of solutions, emulsion, sustained release formulations, or any other form suitable for use.

In some embodiments, the presently disclosed subject matter further provides a method of treating a brain tumor in a subject having or at risk of developing a breast cancer The method comprising administering to the subject a therapeutically effective amount of a composition comprising a RNA nanostructure molecule as disclosed above and herein. In some embodiments, the composition further comprises a pharmaceutically acceptable carrier. In some embodiments, the subject is a mammal or a non-mammal vertebrate. In some embodiments, the subject is a human.

Breast cancer is one of the most common cancers and is often identified as being the second cause of cancer death in women. Breast cancer subtypes are categorized on an immunohistochemical basis, such as normal, luminal A, luminalB, HER2+/ER−, triple-negative, unclassified. (US20120214864, hereby incorporated by reference in its entirety). In the case of triple-negative breast cancer cells, the cancer's growth is not driven by estrogen or progesterone, or by growth signals coming from the HER2 protein. In some embodiments, the breast cancer is triple negative breast cancer.

The term "therapeutically effective amount," as used herein, refers to the amount of a composition containing administered to a patient already suffering from a disease, condition, or disorder, sufficient to cure or at least partially arrest, or relieve to some extent one or more of the symptoms of the disease, disorder, or condition being treated. The effectiveness of such compositions depend upon conditions including, but not limited to, the severity and course of the disease, disorder, or condition, previous therapy, the patient's health status and response to the drugs, and the judgment of the treating physician. By way of example only, therapeutically effective amounts may be determined by routine experimentation, including but not limited to a dose escalation clinical trial.

The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount"; that is, an amount effective for prevention of a disease or condition.

Suitable methods for administering to a subject an effective amount of the composition in accordance with the methods of the present disclosure include but are not limited to systemic administration, parenteral administration (including intravascular, intramuscular, intraarterial administration), oral delivery, buccal delivery, subcutaneous administration, inhalation, intratracheal installation, surgical implantation, transdermal delivery, local injection, and hyper-velocity injection/bombardment. Where applicable, continuous infusion can enhance drug accumulation at a target site (see, e.g., U.S. Pat. No. 6,180,082).

As used herein, the term "subject" refers to a target of administration of the pharmaceutical composition. The subject of the herein disclosed methods can be a vertebrate, such as a mammal, a fish, a bird, a reptile, or an amphibian. Thus, the subject of the herein disclosed methods can be a human or non-human. Thus, veterinary therapeutic uses are provided in accordance with the presently disclosed subject matter. As such, the presently disclosed subject matter provides for administration to mammals such as humans and non-human primates, as well as those mammals of importance due to being endangered, such as Siberian tigers; of economic importance, such as animals raised on farms for consumption by humans; and/or animals of social importance to humans, such as animals kept as pets or in zoos. Examples of such animals include but are not limited to: carnivores such as cats and dogs; swine, including pigs, hogs, and wild boars; ruminants and/or ungulates such as cattle, oxen, sheep, giraffes, deer, goats, bison, and camels; rabbits, guinea pigs, and rodents. Also provided is the treatment of birds, including the treatment of those kinds of birds that are endangered and/or kept in zoos, as well as fowl, and more particularly domesticated fowl, i.e., poultry, such as turkeys, chickens, ducks, geese, guinea fowl, and the like, as they are also of economic importance to humans. Thus, also provided is the treatment of livestock, including, but not limited to, domesticated swine, ruminants, ungulates, horses (including race horses), poultry, and the like. The term does not denote a particular age or sex.

In some embodiments, the present disclosure provide a method of treating breast cancer in a subject having or at risk of having breast cancer. The composition includes administering to the subject a therapeutically effective amount a composition comprising a RNA nanostructure molecule. The RNA nanostructure includes a multiple branched RNA junction motif, a breast cancer targeting module coupled to the RNA junction motif. In some embodiments, the RNA molecule further includes a breast cancer therapeutic agent conjugated to the RNA junction motif. In some embodiments, the composition further includes a pharmaceutically acceptable carrier. The RNA nanostructure molecule is further disclosed as above and throughout this disclosure and further provided below.

In some embodiments of the method, the bioactive agent is a therapeutic agent. The RNA oligonucleotide includes at least one chemical modification at the 2' position. Non-limiting examples of the chemical modification includes 2'Fluoro, 2'Amine, and 2'O-Methyl. In some embodiments, the multiple branched RNA junction motif is a three-branched RNA junction motif. In some embodiments of the method, the RNA molecules form dimers, trimers, hexamers, and patterned superstructures. Exemplary multiple branched RNA sequences include 5'-UUG CCA UGU GUA UGU GGG AUC CCG CGG CCA UGG CGG CCG GGA G-3' (SEQ ID NO: 5), 5'-CCC ACA UAC UUU GUU GAU CCG CCU UAG UAA CGU GCU UUG AUG UCG AUU CGA CAG GAG GC-3' (SEQ ID NO: 6), 5'-GATAAGCT CTC CCG GCC GCC ATG GCC GCG GGA T-3' (SEQ ID NO: 7), 5'-CTC CCG GCC GCC ATG GCC GCG GGA T-3' (SEQ ID NO: 8), and 5'-AUC CCG CGG CCA UGG CGG CCG GGA G-3' (SEQ ID NO: 9). In some embodiments, the diameter of the molecule is at least about 40 nm or less, the molecule has zeta potential ranging from about −100 mV to about 100 mV, and substantially stable in pH from about 2 to about 13. In some embodiments, a branch of the three-branched RNA junction motif includes an a3WJ RNA module (SEQ ID NO: 1), a b3WJ RNA module (SEQ ID NO: 2), or a c3WJ RNA module (SEQ ID NO: 3). In one embodiments, the three-branched RNA junction motif comprises an a3WJ RNA module (SEQ ID NO: 1), a b3WJ RNA module (SEQ ID NO: 2), and a c3WJ RNA module (SEQ ID NO: 3).

In some embodiments of the method, the breast cancer targeting module includes a ligand that binds to at least one breast cancer cell surface marker. In some embodiments, the ligand binds to a folate receptor, an epidermal growth factor receptor 2 (ErbB-2/HER2), an epidermal growth factor receptor (EGFR), a HER2, or a combination thereof. In some embodiments, the ligand is an aptamer. In some embodiments, the aptamer binds to EGFR, PDGFR, folate receptor, or a combination thereof. In some embodiments, the aptamer has sequence 5'-G CCU UAG UAA CGU GCU UUG AUG UCG AUU CGA CAG GAG GQ-3'(SEQ ID NO: 10). In some embodiments, targeting module is a folate. Non-limiting examples of the folate are folic acid, 5-methyltetrahydro folate, 5-formyltetrahydrofolate, dihydrofolate, tetrahydrofolate, or other folate compounds.

In some embodiments, a breast cancer targeting module is coupled to the RNA nanoparticle. The targeting module direct the nanoparticle to the breast cancer cells, to enhance binding to them, to enhance internalization, to enhance targeting to cellular enzymes, DNA, RNA, proteins, lipids, or carbohydrates. Non-limiting examples of the breast cancer targeting module are antibodies, antibody fragments, polypeptides, cell ligands, aptamers, DNA, RNA, drugs, compounds that enhance targeting the breast cancer cell, and other groups or materials that enhance binding to breast cancer cells.

In some embodiments of the method, the presently disclosed subject matter provides that the bioactive agent is a therapeutic agent. In some embodiments, the bioactive agent is a drug, a fluorescent dye, or a chemical, or a combination thereof. In some embodiments, the bioactive agent is a siRNA, a miRNA, an anti-miRNA, a ribozyme RNAs, an antisense RNAs. In some embodiments, the bioactive agent is directed to a breast cancer marker. In some embodiments, the bioactive agent is a siRNA sequence or a microRNA sequence. In some embodiments, the siRNA binds to a mRNA molecule of an oncogene. Non-limiting oncogene includes RAS, cMET, HER2, MDM2, PIK3CA, AKT, CDK4, or a combination thereof.

In further embodiments of the method, the bioactive agent is an anti-miRNA molecule for a miRNA to interfere with miRNA to regress cancer growth. Non-limiting example of miRNA includes miR-9, miR-10b, miR-21, miR-17, and miR-26. In some embodiments, the RNA nanostructure molecule introduces tumor suppressive miRNAs to rescue down-regulated tumor suppressive miRNAs. Non-limiting examples of the miRNA include let-7a, miR-10b, miR-25, miR-34a, miR-124, miR-145, and miR-181b. In one embodiment of the method, the microRNA sequence is an anti-miR-21 sequence. In some embodiments, non-limiting examples of the miRNA sequence comprises 5'-GA-TAAGCT-3' (SEQ ID NO: 11), 5'-AGCACTTT-3', or 5'-AT-TTGCAC-3'. In some embodiments, the miRNA is a LNA miRNA sequence. Non-limiting examples of the LNA miRNA sequences are 5'-+G+A+T+A+A+G+C+T-3' (SEQ ID NO: 11), 5'-+A+G+C+A+C+T+T+T-3', or 5'-+A+T+T+T+G+C+A+C-3'. In some embodiments, the RNA nanostructure inhibit breast cancer cells proliferation.

In one embodiments, multi-functional RNA nanoparticles are constructed using the three-way junction (3WJ) motif (FIG. 1) (38,39,48,49) derived from bacteriophage phi29 packaging RNA (pRNA) (50) as a scaffold harboring (a) RNA aptamers as targeting ligands; (b) therapeutic anti-miRNAs; and (c) fluorescent imaging module—Alexa647. To precisely guide and internalize the therapeutic anti-miRNAs to TNBC cells, epidermal growth factor receptor (EGFR) targeting RNA aptamers are used (51). EGFR is highly amplified (>97%) in both primary TNBC tumors and metastatic TNBC cells (52,53). As the therapeutic target, the present disclosure focuses on oncogenic miR-21, which is maintained throughout tumor initiation, progression, invasion, and metastasis in varieties of solid cancers, including TNBC (54-58). Orthotopic TNBC tumors is established in nude mice and then systemically administered the multi-functional RNA nanoparticles to determine their targeting and therapeutic effects.

The presently disclosed subject matter is further illustrated by the following specific but non-limiting examples. The following examples may include compilations of data that are representative of data gathered at various times during the course of development and experimentation related to the present disclosure.

EXAMPLES

This study provides that MicroRNAs play important roles in regulating the gene expression and life cycle of cancer cells. In particular, miR-21, an oncogenic miRNA is a major player involved in tumor initiation, progression, invasion and metastasis in several cancers, including triple negative breast cancer (TNBC). However, delivery of therapeutic miRNA or anti-miRNA specifically into cancer cells in vivo without collateral damage to healthy cells remains challenging. It is report here the application of RNA nanotechnology for specific and efficient delivery of anti-miR-21 to block the growth of TNBC in orthotropic mouse models. The 15-nm therapeutic RNA nanoparticles contains the 58-nucleotide (nt) phi29 pRNA-3WJ as a core, a 8-nt sequence complementary to the seed region of miR-21, and the 39-nt anti-epidermal growth factor receptor (EGFR) aptamer for internalizing RNA nanoparticles into cancer cells via receptor medicated endocytosis. The RNase resistant and thermodynamically stable RNA nanoparticles remained intact after systemic injection into mice and strongly bound to tumors with little or no accumulation in healthy organs eight hours post-injection, and subsequently repressed tumor growth at low doses. The observed specific cancer targeting and tumor regression is a result of several key attributes of RNA nanoparticles: anionic charge which disallows nonspecific passage across negatively charged cell membrane; 'active' targeting using RNA aptamers which increases the homing of RNA nanoparticles to cancer cells; nanoscale size and shape which avoids rapid renal clearance and engulfment by lung macrophages and liver Kupffer cells; favorable biodistribution profiles with little accumulation in healthy organs, which minimizes non-specific side effects; and favorable pharmacokinetic profiles with extended in vivo half-life. The results demonstrate the clinical potentials of RNA nanotechnology based platform to deliver miRNA based therapeutics for cancer treatment.

Construction and Characterization of Triple-Functional pRNA-3WJ Nanoparticles

Figure 2:
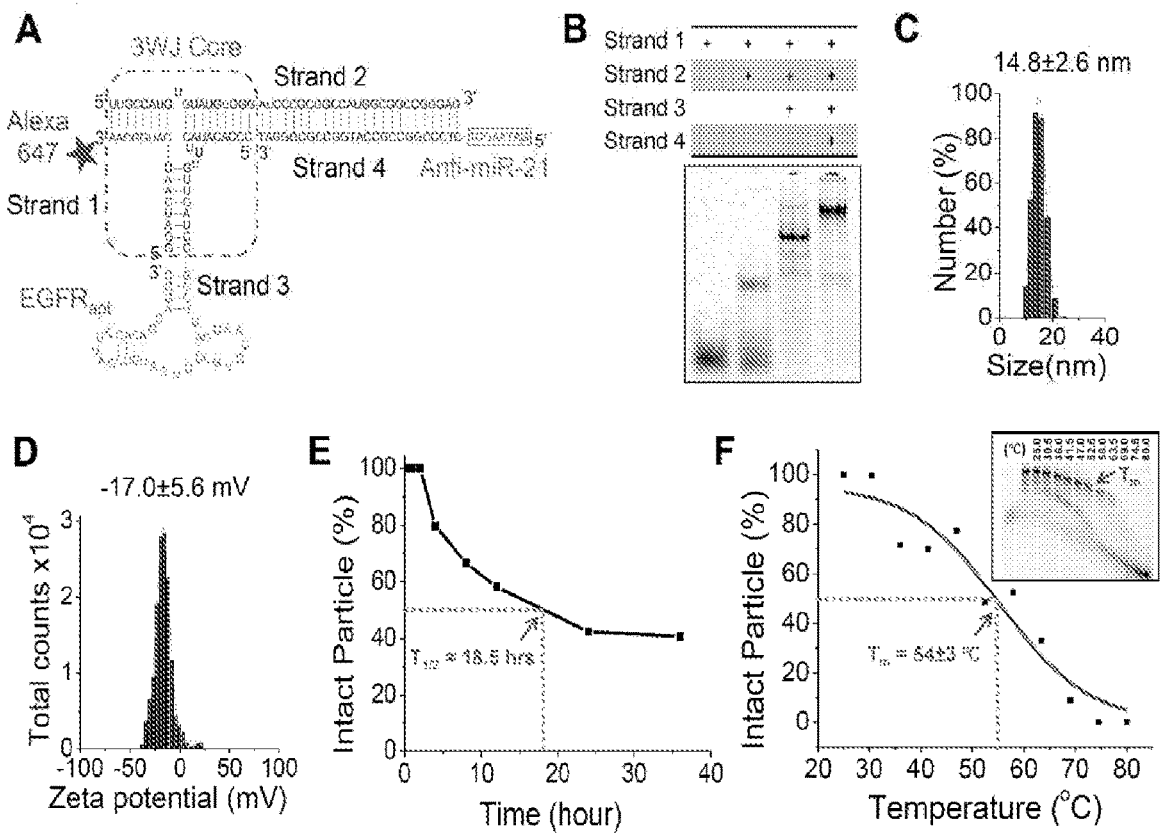
FIGS. 2A-2F show design and physicochemical characterization of 3WJ-EGFRapt/anti-miR-21 nanoparticles.

The pRNA-3WJ nanoparticles utilize a modular design composed of three short fragments (FIG. 1A).[38] Upon mixing the individual strands in equal molar ratio in PBS or TMS buffer, the complex assembles with high efficiency, as shown in previous publications.[38,39,48,59] Each branch of the pRNA-3WJ can harbor a functional module without interfering with the folding of the core scaffold and the function of each module, as demonstrated by atomic force microscopy (AFM) images showing homogeneous triangular branched architectures (FIG. 1B-C). Herein, the pRNA-3WJ core are used as a scaffold and constructed tri-functional RNA nanoparticles 3WJ-EGFRapt/anti-miR-21, harboring EGFR targeting RNA aptamer, therapeutic anti-miR-21 and Alexa-647 as imaging module (FIG. 2A). When the four strands were mixed in stoichiometric ratio, the RNA nanoparticle assembled with very high efficiency as indicated by gel shift assays showing step-wise assembly of the complex (FIG. 2B).

Dynamic light scattering (DLS) assays showed that the average hydrodynamic diameter of 3WJ-EGFRapt/anti-miR-21 nanoparticles was 14.8±2.6 nm (FIG. 2C) compared to 4.2±1.1 nm for pRNA-3WJ core scaffold (FIG. 1D). It is noted that the 3WJ-EGFRapt/anti-miR-21 nanoparticle is not globular in shape, and deviations from DLS measurements are expected, since the reported DLS size corresponds to the average of the three dimensions due to rapid tumbling of RNA nanoparticles in solution.

The particle surface charge, zeta potential, was determined to evaluate the aggregation propensity of RNA nanoparticles in solution. RNA nanoparticles are indeed highly negatively charged and do not aggregate in solution, and this is reflected in the zeta potential measurements showing a single peak at −16.1±7.7 mV for pRNA-3WJ core scaffold (FIG. 1E) and −17.0±5.6 mV for 3WJ-EGFRapt/anti-miR-21 nanoparticles (FIG. 2D). This aggregation-free physical property and anionic nature is particularly attractive for in vivo delivery applications, since it minimizes non-specific cell entry, and entrapment by lung macrophages and liver Kupffer cells (11).

To make the 3WJ-EGFRapt/anti-miR-21 nanoparticle chemically stable in vivo, 2'-F modified U and C nucleotides are used (60-61). The 2'-F modified RNA nanoparticles were incubated with 50% fetal bovine serum (FBS) at 37° C. At defined time points, samples were collected and assayed using native PAGE gel (FIG. 2E). The fraction of intact RNA nanoparticles was quantified using ImageJ software and plotted to determine a half-life of about 15 hrs, which is significantly higher than the half life of unmodified RNA counterparts.[38,60] The presence of 2'-F nucleotides not only makes the RNA nanoparticles resistant to RNase degradation, but also enhances the melting temperature of pRNA-3WJ,[40] without compromising the authentic folding and functionalities of the core and incorporated modules.[37,38]

The 2'-F modified 3WJ-EGFRapt/anti-miR-21 nanoparticles were subjected to temperature gradient gel electrophoresis (TGGE) assay, typically used to determine one of the thermodynamic parameters, the apparent melting temperature ($T_m$), of RNA nanoparticles composed of multiple strands.[41,48,62,63] One of the strands was labeled with Alexa-647, which was used to determine the fraction of intact particles remaining with increasing temperature gradient (from 25° C.→80° C.) applied perpendicular to the electric current (FIG. 2F, boxed). The fraction of RNA assembled was quantified using ImageJ software and the melting curve was fitted with non-linear sigmoidal fitting to determine an apparent $T_m$ of 54±3° C. (FIG. 2F). The results indicate that the constructed RNA nanoparticle with all the functional modules are thermostable and will remain structurally intact at ultra-low concentrations in the body.

Binding and Internalization of pRNA-3WJ Nanoparticles into TNBC Cells

Figure 3:
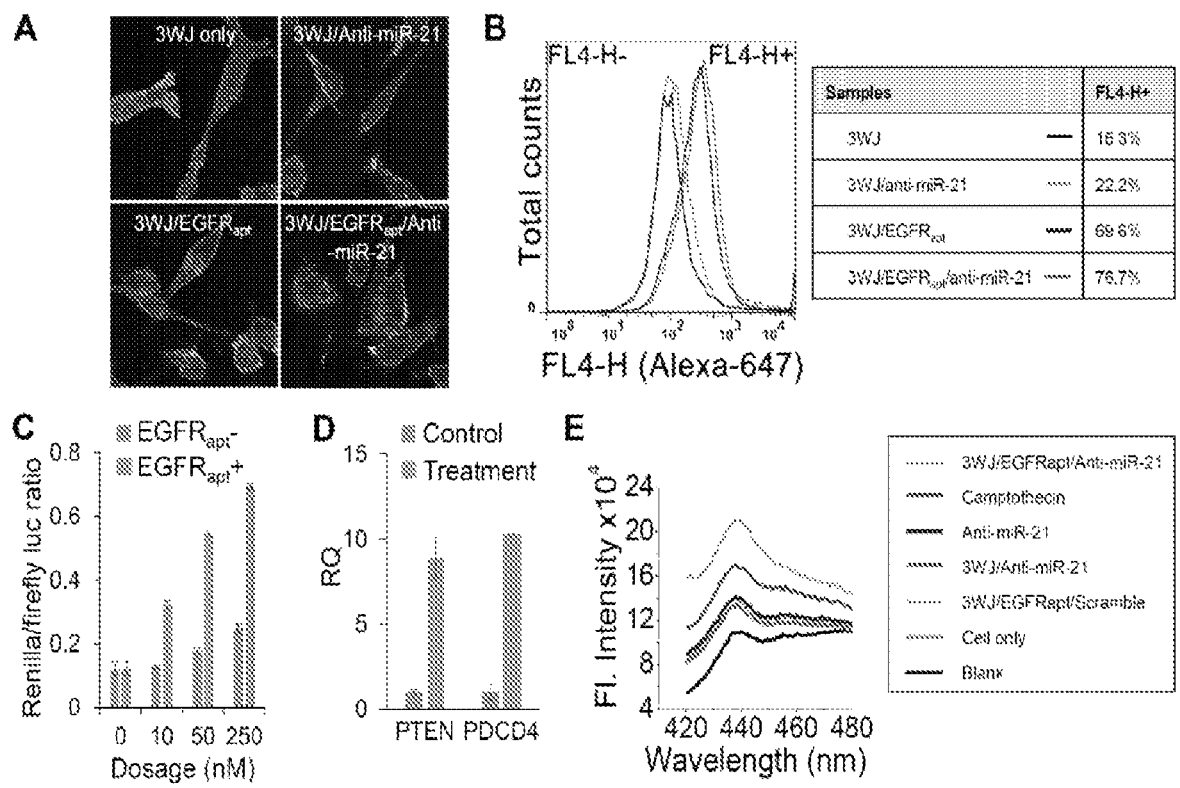
FIGS. 3A-3E include graphs and images showing the evaluation of targeting and therapeutic effects of 3WJ-EGFRapt/anti-miR-21 nanoparticles in vitro.

Alexa647 labeled 3WJ-EGFRapt/anti-miR-21 nanoparticles were incubated with MDA-MB-231 cells. The cells were then fixed with paraformaldehyde, and the nuclei and cytoplasm were stained using DAPI and Alexa488-phalloidin, respectively. Confocal microscopy images showed very efficient binding and internalization of pRNA-3WJ nanoparticles into cancer cells through EGFR mediated endocytosis, as demonstrated by excellent overlap of fluorescent RNA nanoparticles (red color in FIG. 3A) and cytoplasm (green color in FIG. 3A). Very low signal was observed for control groups (3WJ scaffold only and 3WJ-anti-miR-21 without EGFR RNA aptamer). The results were further validated using Fluorescence-Activated Cell Sorting (FACS) assay (FIG. 3B). The 3WJ-EGFRapt/anti-miR-21 nanoparticles (and controls) were incubated with MDA-MB-231 cells, washed and then analyzed by FACS. Strong binding (76.7%) was observed for EGFR RNA aptamer bearing RNA nanoparticles compared to pRNA-3WJ scaffold control (16.3% binding) (FIG. 3B). The results indicate that these RNA nanoparticles have high specificity and affinity for TNBC cell binding.

Delivery of Anti-miR-21 to TNBC Cells by pRNA-3WJ Nanoparticles

It was next tested the specific knockdown of oncogenic miR-21 in MDA-MB-231 cells, known to express high levels of miR-21.[57] As anti-miR-21 agent, 8-mer (5'GA-TAAGCT-3') (SEQ ID NO: 11) locked nucleic acid (LNA, conformationally restricted nucleotide analogs) that is complementary to the miR-21 seed region is used(64). LNAs have been reported to bind to their complementary miRNAs with very high affinity and specificity, and are also resistant to exo-/endo-nucleases.[61,65] Upon binding to the miRNA seed region, LNAs will trigger miRNA inhibition in a dose dependent manner.[64]

For assaying miR-21 inhibition, a very sensitive luciferase-based miR-21 reporter system is developed. MDA-MB-231 cells were transfected with a reporter plasmid which contains a miR-21 targeting sequences at the 3'-untranslated regions (UTR) region of *Renilla* Luciferase gene and a co-expressed Firefly Luciferase gene as the internal control. In native cells, the *Renilla* expression would be repressed, as the miR-21 bind to its 3'-UTR region and prevent the translation of *Renilla* Luciferase. As anti-miRNA LNA are delivered into the cancer cells, the LNA sequence will competitively bind to miR-21 that used to bind to 3'-UTR region of *Renilla* Luciferase gene and block its translation, thus resulting in an increased expression of *Renilla* Luciferase. The results demonstrated that 3WJ-EGFRapt/anti-miR-21 effectively delivered anti-miR-21 LNA sequence into MDA-MB-231 cells after incubation, as indicated by increased *Renilla* Luciferase expression in a dose dependent manner compared to the control 3WJ-anti-miR-21 nanoparticle without EGFR aptamer (FIG. 3C). The successful delivery via incubation with cancer cells is a significant advancement in RNAi-based cancer therapeutics, since RNA therapeutics are typically delivered by transfection or microporation methods.

The functionality of miR-21 was validated on its downstream target tumor suppressors, PTEN and PDCD4 genes.[55-57] After incubation with MDA-MB-231 cells, 3WJ-EGFRapt/anti-miR-21 nanoparticles up-regulated the expression of both PTEN and PDCD4, assayed by qRT-PCR at the mRNA levels compared to control 3WJ-anti-miR-21 without EGFR aptamer (FIG. 3D).

Effects of pRNA-3WJ Nanoparticles on Growth and Apoptosis of TNBC Cells

Caspase-3 (cysteinyl aspartate-specific protease-3) is an early cellular apoptotic marker, and its activation can be used to assess whether cells are undergoing apoptosis. 3WJ-EGFRapt/anti-miR-21 treated MDA-MB-231 cell lysates showed the highest fluorescence emission of caspase-3 fluorogenic substrate (Ac-DEVD-AMC ("DEVD" disclosed as SEQ ID NO: 23)) comparable to the positive control camptothecin (CPT), and in contrast to the control RNAs (anti-miR21, 3WJ-anti-miR21, and 3WJ-EGFRapt/Scramble). The results indicate that 3WJ-EGFRapt/anti-miR-21 nanoparticles can activate caspase-3 pathway and trigger cancer cell apoptosis (FIG. 3E).

Figure 4:
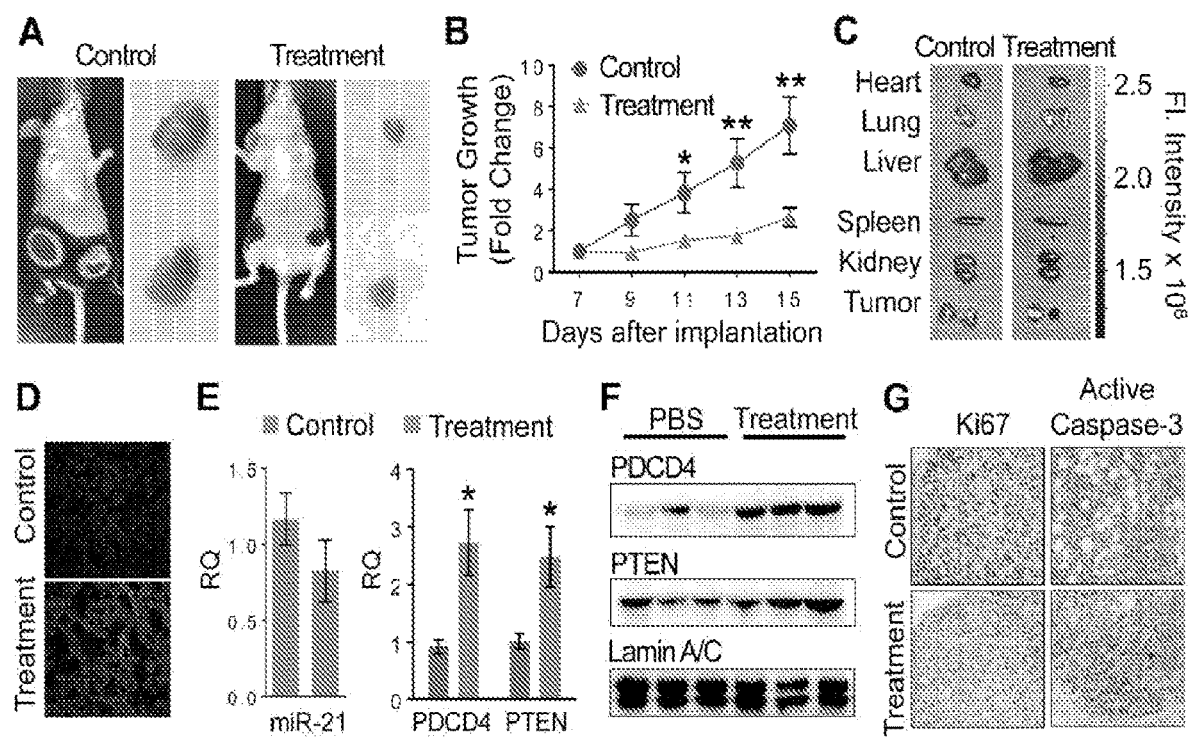
FIGS. 4A-4F are images and graphs showing the evaluation of targeting and therapeutic effects of 3WJ-EGFRapt/anti-miR-21 nanoparticles using orthotropic TNBC mouse model.
FIG. 4G includes images showing immunohistochemistry assay showing inhibition of tumor cell growth after treatment, using Ki67 as indicator of tumor cell proliferation, and caspase-3 as indicator of tumor cell apoptosis.

Specific Targeting of TNBC Tumors in Animal Models Assessed by Fluorescence Imaging of RNA Nanoparticles To evaluate tumor targeting, 3WJ-EGFRapt/anti-miR-21 nanoparticles were systemically administered via the tail vein into orthotopic TNBC tumor bearing mice. Ex vivo images of normal tissues, organs, and tumors taken after 8 hrs showed that RNA nanoparticles specifically targeted and accumulated in the tumors, and little or no accumulation was observed in healthy organs and tissues (FIG. 4C). In terms of tumor accumulation kinetics, RNA nanoparticles reached their highest accumulation 8 hrs post-injection and remained in the tumor thereafter for an extended period of time to trigger miRNA knockdown. Such distinct tumor retention behavior is due to the nanoscale size and shape of RNA nanoparticles that are favorable for enhanced permeability and retention (EPR) effects. Histological profiles of breast tumor sections revealed that 'active' targeting 3WJ-EGFRapt/anti-miR21 nanoparticles (mediated by EGFR targeting RNA aptamers) strongly bound and internalized into cancer cells, as shown by strong association of RNA nanoparticles (red) with counterstained TNBC cells (FIG. 4D).

RNA Nanoparticles for In Vivo Targeted Delivery of Anti-miRNA to TNBC Cells

Orthotopic TNBC tumors are developed in nude mice using MDA-MB-231 cells expressing luciferase. Upon systemic injection of luciferin, the cancer cells are visualized using bioluminescence imaging to measure the tumor size and quantitatively assess whether the systemically delivered 3WJ-EGFRapt/anti-miR-21 nanoparticles can down-regulate miR-21 and in the process inhibit tumor growth. TNBC tumor-bearing mice were injected with 3WJ-EGFRapt/anti-miR-21 nanoparticles for 5 times every other day, and the luminescence signal was measured to assess luciferase activity. The end point luminescence signal after 5 doses (15 days) from the mice treated with 3WJ-EGFRapt/anti-miR-21 RNA nanoparticle were significantly lower than the control treated mice (FIG. 4A). This was also evident in the tumor growth curve showing sustained inhibition of tumor growth by 3WJ-EGFRapt/anti-miR-21 nanoparticles compared to the vehicle control (FIG. 4B).

To validate anti-miR-21 knockdown at the molecular level, tumor tissues were extracted and lysed. The miR-21 as well as its downstream target mRNAs of PTEN and PDCD4 were quantified by qRT-PCR assay at the mRNA level, and the expression of PTEN and PDCD4 was also examined by Western blot assay at the protein level. The data showed that 3WJ-EGFRapt/anti-miR-21 nanoparticles treated tumors have reduced miR-21 levels compared to control group (FIG. 4E, left panel). The knockdown of miR-21 correlated with increased expression of both PTEN and PDCD4 at both mRNA (FIG. 4E, right panel) and protein levels (FIG. 4F) for the treatment group compared to the control group. Furthermore, 3WJ-EGFRapt/anti-miR-21 RNA nanoparticle treatment reduced cell proliferation in the tumor tissue, as revealed by decreased Ki67 staining (FIG. 4G, left panel), and induced cancer cell apoptosis, as indicated by increased caspase-3 levels (FIG. 4G, right panel), compared to the control group.

CONCLUSIONS

Since the discovery of RNAi as a key post-transcriptional gene regulation mechanism,[66] it has been proposed for a long time as a potential cancer treatment strategy.[67-73] However, due to the lack of a safe and efficient delivery system, the therapeutic small RNAs including siRNA, miRNA, anti-miRNA and splice-switching oligonucelotides behave poorly in vivo. Due to their small size (hydrodynamic diameters typically <5 nm), these small therapeutic RNAs display very short half-life to efficiently trigger their target knockdown[42,74] as they are rapidly cleared by the kidneys.[75] This shortcoming has significantly hindered the clinical translation of RNAi based reagents for disease treatment. Therefore, an effective RNAi delivery system, which can increase the size of the small RNAs as well as introduce cancer specific targeting moieties using cancer cell binding ligands will significantly enhance the pharmacokinetic and therapeutic efficacies of these small therapeutic RNAs.

The construction of RNA nanoparticles is studied here using the pRNA-3WJ core for specific targeting and delivery of anti-miRNA to cancer cells in vivo. The data indicated that upon systemic injection in orthotopic TNBC tumor bearing mice, 3WJ-EGFRapt/anti-miR-21 nanoparticles can navigate across heterogeneous biological barriers surrounding the tumors to specifically bind and internalize into TNBC cells, knockdown miR-21 resulting in upregulation of PTEN and PDCD4, and efficiently inhibit tumor growth. Moreover, biodistribution studies in vivo showed that the RNA nanoparticles can specifically target tumors with little or no accumulation in healthy organs and tissues, which is a significant accomplishment in cancer therapeutics. Specific cancer targeting is a direct result of the RNA nanoparticles physiochemical properties, such as homogeneous size and structure; highly negative charge which minimizes aggregation propensity and nonspecific entry across negatively charged cell membrane; multivalency to enable combined therapy, targeting and detection, all in one platform; targeted delivery into cancer cells via receptor mediated endocytosis using RNA aptamers; advantageous size for favorable biodistribution profiles; extended in vivo half-life (5-12 hr compared to 0.25-0.75 hr for bare anti-miRNA); and non-toxic and non-immunogenic nature.[42] RNA nanoparticles are chemical drugs rather than biological entities, which will facilitate FDA approval process. Taken together, The data demonstrated that pRNA-3WJ nanoparticles have the potential to be applied for clinical applications as a targeted therapeutic delivery system to treat cancer in vivo. Due to the ease and flexibility of modification on each RNA module, in the future, different drugs, siRNAs, miRNAs or anti-miRNAs can be incorporated into the RNA nanoparticles as therapeutic functionalities for the treatment of different diseases.

METHODS AND EXPERIMENTAL

Design and Construction of 2'-F Modified pRNA-3WJ Nanoparticles

Multifunctional pRNA-3WJ nanoparticles were constructed using a bottom-up self-assembly approach.[38] The 3WJ-EGFRapt/anti-miR-21 consisted of four fragments (FIG. 2A) harboring EGFR targeting RNA aptamer (EGFRapt) as a targeting ligand; AlexaFluor® 647 (Invitrogen), as a fluorescent imaging module; and anti-miRNA-21 LNA (anti-miR-21) (Exiqon), as a therapeutic module. The controls include RNA nanoparticles without targeting ligand (denoted as 3WJ-anti-miR-21); without therapeutic module (denoted as 3WJ-EGFRapt), or without therapeutic and targeting modules (denoted as 3WJ).

The core sequences of pRNA-3WJ are (FIG. 1A):

$a_{3WJ}$:
(SEQ ID NO: 1)
5'-UUG CCA UGU GUA UGU GGG-3';

$b_{3WJ}$:
(SEQ ID NO: 2)
5'-CCC ACA UAC UUU GUU GAU CC-3';

$c_{3WJ}$:
(SEQ ID NO: 3)
5'-GGA UCA AUC AUG GCA A-3'.

The therapeutic 3WJ-EGFRapt/anti-miR-21 is composed of four strands (FIG. 2A). Lowercase letters indicate 2'-F modified nucleotides:

Strand 1:
(SEQ ID NO: 4)
5'-GGA ucA Auc AuG GcA A (C6-NH)(Alexa 647)-3';

Strand 2:
(SEQ ID NO: 5)
5'-uuG ccA uGu GuA uGu GGG Auc ccG cGG ccA uGG cGG ccG GGA G-3';

Strand 3:
(SEQ ID NO: 6)
5'-ccc AcA uAc uuu Guu GAu ccG ccu uAG uAA cGu Gcu uuG AuG ucG Auu cGA cAG GAG Gc-3' (underlined sequence is EGFR aptamer[51]);

Strand 4:
(SEQ ID NO: 7)
5'-+ G + A + T + A + A + G + C + T CTC CCG GCC GCC ATG GCC GCG GGA T-3' (underlined sequence is 8-mer anti-miR21 LNA);

The RNA fragments were synthesized chemically (Trilink and Exiqon) and strands 1-3 are 2'-F modified at cytosine (C) and uracil (U) nucleotides to make the RNA nanoparticles resistant to RNase degradation. The pRNA-3WJ nanoparticles were assembled by mixing the four strands at equal molar concentrations in annealing buffer (10 mM Tris, pH 7.5-8.0, 50 mM NaCl, 1 mM EDTA), and heated to 95° C. for 5 minutes and slowly cooled to 4° C. over 45 minutes. Step-wise assembly of the RNA nanoparticles was verified on a native 10% PAGE running in 1×TBE (89 mM Tris-borate, 2 mM EDTA) buffer and imaged by Typhoon FLA 7000 (GE Healthcare) under Cy5 channel.

Characterization of the Assembled pRNA-3WJ Nanoparticle

The assembly of the functionalized 3WJ nanoparticles was characterized by native poly-acrylamide gel electrophoresis (PAGE) assays followed by imaging by Typhoon FLA 7000 (GE Healthcare). The structures of the assembled 3WJ complexes were assessed by atomic force microscopy (AFM), and dynamic light scattering (DLS) as described previously (38, 76-78). RNA images (FIG. 1C) were generated using specially modified mica surfaces (APS mica) and imaged with a Veeco MultiMode AFM NanoScope IV system, operating in tapping mode (77). DLS measurement revealed that the size of the 3WJ core (FIG. 1A) was 4.2±1.1 nm (FIG. 1D), and the size of the 3WJ-EGFRapt/anti-miR-21 nanoparticle (FIG. 2A) was 14.8±2.6 nm (FIG. 2C). Due to the resolution limit of AFM image affected by the tip size of 4-10 nm, the size of 3WJ core and 3WJ-EGFRapt/ant-miR-21 nanoparticle were too small to reveal the detail structure and shape. To evaluate the global structures of the RNA nanoparticles derived from the 3WJ core, of which the crystal structure has been solved, 58-60 bp of dsRNA was extended to the three arms of the 3WJ core (FIG. 1B) (49). It is expected that 58-60 bp is within the persistence length (stiffness) of 229 bp, thus the AFM image of the resulting arm-extended RNA nanoparticle (FIG. 1C) is expected to provide some information about the global structure of RNA nanoparticles derived from the thermodynamically stable 3WJ (79). Apparent hydrodynamic sizes and zeta potential of pre-assembled 3WJ (1.5 μM in DEPC $H_2O$) and 3WJ-EGFRapt/anti-miR-21 (1.35 μM in TBE buffer) were measured by Zetasizer nano-ZS (Malvern Instrument, LTD) at 25° C., respectively. The data were obtained from three independent measurements.

Temperature Gradient Gel Electrophoresis (TGGE) Assay

The thermodynamic stability of the 2'-F modified 3WJ-EGFRapt/anti-miR-21 nanoparticles was studied using the TGGE system (Biometra GmbH, Germany). One of the fragments ($c_{3WJ}$) was 3'-end labeled with Alexa647 prior to the assembly of the complex. The 3WJ-EGFRapt/anti-miR-21 nanoparticles were subjected to a 10% native PAGE (2.5 uL of 1 μM RNA nanoparticles per well) and allowed to run in TBM buffer (89 mM Tris, 200 mM boric acid, and 2.5 mM $MgCl_2$) for 5 min at ambient temperature at constant 100 V. After running the RNA into the gel matrix, the gel was transferred into TGGE apparatus and a linear temperature gradient was set up from 25 to 80° C. perpendicular to the electrical current. The gel was run at 80 V for 90 minutes, and then imaged by Typhoon FLA 7000 (GE Healthcare). The intact particle fraction within the total RNA was analyzed by ImageJ, and the melting curve of the construct was fitted using nonlinear sigmoidal fitting. The apparent $T_m$ of the pRNA-3WJ nanoparticle was determined as the temperature at which 50% of the RNA nanoparticle remained assembled.

Serum Stability Assay

The chemical stability of 3WJ-EGFRapt/anti-miR-21 nanoparticles was studied by incubating the RNA nanoparticle with 50% fetal bovine serum (FBS) at 37° C. at final concentration of 2 μM. 10 uL of samples were collected at each time point (0, 0.5 h, 1 h, 2 h, 4 h, 8 h, 12 h, 24 h, and 36 h) and were subjected to a 10% native PAGE assay with TBM running buffer. The gel was run at 120 V for 120 minutes, and then imaged by Typhoon FLA 7000 (GE Healthcare). The fraction of intact nanoparticle within the total RNA was analyzed and quantified by ImageJ.

Cell Culture

Human TNBC cell line MDA-MB-231 (American Type Culture Collection, ATCC) and MDA-MB-231-Luc (expressing luciferase reporter gene) were grown and cultured in DME/F-12 (1:1) medium (Thermo Scientific) containing 10% FBS inside a 37° C. incubator with 5% $CO_2$ and a humidified atmosphere.

In Vitro Binding Assay Using Fluorescence-Activated Cell Sorting (FACS)

MDA-MB-231 cells were trypsinized and rinsed with blank DME/F-12 (1:1) medium. 100 nM Alexa647 labeled 3WJ-EGFRapt/anti-miR-21 and the control RNA nanoparticles without EGFR aptamer were each incubated with $2 \times 10^5$ MDA-MB-231 cells at 37° C. for 2 hr. After washing with PBS (137 mM NaCl, 2.7 mM KCl, 100 mM $Na_2HPO_4$, 2 mM $KH_2PO_4$, pH 7.4), the cells were resuspended in PBS buffer. FACS was performed using Flow Cytometer (Becton, Dickinson) (available at the University of Kentucky Markey Cancer Center Flow Cytometry and Cell Sorting core facility) to observe the cell binding efficiency of the RNA nanoparticles. The data were analyzed by FlowJo 7.6.1 software.

In Vitro Binding and Internalization Assay Using Confocal Microscopy Imaging

MDA-MB-231 cells were grown on Lab-TekII 8-well chamber slide (Nunc) in DME/F-12 (1:1) medium overnight. 100 nM concentration of Alexa647 labeled 3WJ-EGFRapt/anti-miR-21 and the control 3WJ, 3WJ-EGFRapt, and 3WJ-anti-miR-21 were each incubated with the cells at 37° C. for 2 hrs. After washing with PBS, the cells were fixed by 4% paraformaldehyde (PFA) and washed 3 times by PBS. The cytoskeleton of the fixed cells was stained by Alexa488 Phalloidin (Life Technologies) for 30 min at room temperature and then rinsed with PBS for 3×10 min. The cells were mounted with Prolong® Gold antifade reagent. DAPI (Life Technologies) was used for staining the nucleus. The cells were then assayed for nanoparticles binding and cellular entry by FluoView FV1000-Filter Confocal Microscope System (Olympus) (available at the University of Kentucky Markey Cancer Center imaging core facility).

Dual Luciferase Assay to Analyze Delivery of Anti-miR-21 by pRNA-3WJ Nanoparticles MDA-MB-231 cells were grown on 24-well plates in DME/F-12 (1:1) medium until they reached 80% confluence. Cells were transfected with 150 ng psi-Check 2 plasmid (Promega) which contains an oncogenic miR-21 binding sequences at the 3'-UTR region of *Renilla Luciferase* gene using *Lipofectamine* 2000 (Life Technologies). 4 hrs after transfection, the medium was replaced with complete DME/F-12 (1:1) medium and the cells were incubated for another 2 hrs. Various concentration of 3WJ-EGFRapt/anti-miR-21 and the control RNA 3WJ-anti-miR-21 (0, 10, 50, 250 nM) were then incubated with cells in opti-MEM at 37° C. for 2 h, respectively. After incubation with the RNA, complete DME/F-12 (1:1) medium was added into cells and Duel-luciferase assay (Promega) was used to evaluate the anti-miR-21 effects 24 hrs post-transfection following manufacturer's instruction. Briefly, cells were washed once with PBS and lysed with passive lysis buffer. The cell culture plates were shaken for 15 mins at room temperature. 20 μL of the lysate were added to 50 μL of luciferase assay reagent (LAR II) in 96-well plates and control firefly luciferase activity was measured. Upon addition of 50 μL of Stop & Glo Reagent, measurements of *Renilla* luciferase activity were then obtained. The *Renilla* luciferase activity was then normalized with respect to the firefly luciferase activity for determining the relative ratio of *Renilla* to firefly luciferase activity. At least three independent experiments were performed.

Assay the Effects of RNA Nanoparticles on TNBC Cells in Cell Cultures Using qRT-PCR MDA-MB-231 cells were incubated with 100 nM of the 3WJ-EGFRapt/anti-miR-21 and control RNA nanoparticles, respectively. After 72 hrs treatment, cells were collected and target gene up-regulation effects were assessed by qRT-PCR at the mRNA level. Cells were processed for total RNA using Trizol RNA extraction reagent following manufacturer's instruction (Life Technologies).

To assay the miR-21 down-regulation, the TaqMan® microRNA Assays were performed according to manufacturer's instruction (Life Technologies). Briefly, 10 ng total RNA was used to perform the reverse transcription using TaqMan® MicroRNA Reverse Transcription Kit (Life Technologies). MiR-21 specific RT primers were used. Real-time PCR was performed using Taqman Assay. All reactions were carried out in a final volume of 20 μl using Taqman Universal PCR Master Mix and assayed in triplicates. Primers/probe set for human miR-21, and U6 (endogenous control) were purchased from Life Technologies. PCR was performed on StepOne™/StepOnePlus™ systems (Applied Biosystems). The data was analyzed by the comparative CT Method (ΔΔCT Method).

To assay the downstream target genes (PTEN and PDCD4) of miR-21, TaqMan® Gene Expression Assays was performed according to manufacturer's instruction (Life Technologies). Briefly, the first cDNA strand was synthesized from total RNA (1 m) using SuperScript™ III First-Strand Synthesis System (Life Technologies) from MDA-MB-231 cells with the various RNA nanoparticles treatment. Real-time PCR was performed using Taqman Assay. All reactions were carried out in a final volume of 20 μl using 2×Taqman Fast Universal PCR Master Mix and assayed in triplicate. Primers/probe set for human PTEN, PDCD4, and 18S (endogenous control) were purchased from Life Technologies. PCR was performed on StepOne™/StepOnePlus™ systems (Applied Biosystem). The data was analyzed by the comparative CT Method (ΔΔCT Method).

Apoptosis Studies in Cell Culture

In order to assay the cellular effects after RNA nanoparticle treatment, MDA-MB-231 cells were grown on 24-well plates in DME/F-12 (1:1) medium until they reached 80% confluence. Cells were then treated with 100 nM 3WJ-EGFRapt/anti-miR-21. The controls include anti-miR-21, 3WJ-anti-miR-21, and 3WJ-EGFRapt/Scramble. 24 hrs after incubation with the RNAs, the cellular Caspase-3 activity was measured and compared by Caspase-3 Assay Kit (BD Pharmingen) according to manufacturer's instruction. Briefly, cell lysates ($1$-$10 \times 10^6$ cells/ml) after induction of apoptosis were prepared using cold cell lysis buffer provided by the kit, and incubated for 30 mins on ice. For each sample, 50 μL of cell lysate was added with 5 μL reconstituted Ac-DEVD-AMC ("DEVD" disclosed as SEQ ID NO: 23) in HEPES buffer and incubated at 37° C. for 1 hr. The amount of AMC liberated from Ac-DEVD-AMC ("DEVD" disclosed as SEQ ID NO: 23) was measured using an excitation wavelength of 380 nm and an emission wavelength range of 420-460 nm on Fluorolog fluoro-spectrometer (Horiba Jobin Yvon). Camptothecin (CPT) was used as a positive control, which was added into cell culture medium 4 hrs prior to the analysis of the caspase-3 activity.

Animal Models

All protocols involving animals are performed under the supervision of the University of Kentucky Institutional Animal Care and Use Committee (IACUC). To generate TNBC orthotropic model, female athymic nu/nu mice, 4-8 weeks old, were purchased from Taconic laboratories. Orthotopic tumor xenografts was established by directly injecting $2 \times 10^6$ MDA-MB-231-Luc cells resuspended in PBS into the mammary fat pad of nude mice. When the tumor showed sign of growth, the mice were used for assaying therapeutic effects. When the tumor nodules had reached a volume of 100 mm³ approximately 15 days post-injection, the mice were used for tumor targeting studies.

Fluorescence Imaging to Detect the Binding of RNA Nanoparticles to Orthotopic TNBC Xenografts In Vivo To investigate the delivery of pRNA-3WJ nanoparticles in vivo, a fluorescence imaging study was performed after tail vein injection of 100 μL 20 uM Alexa647 labeled 3WJ-EGFRapt/anti-miR-21 into orthotopic TNBC tumor mice. PBS injected mice were used as fluorescence negative control, The mice were sacrificed at 8 hrs post injection by inhalation of $CO_2$ followed by cervical dislocation, and major internal organs including heart, lungs, liver, spleen, kidneys together with tumor from the sacrificed mice were collected and subjected to fluorescence imaging for assessment of biodistribution profile using IVIS Spectrum station (Caliper Life Sciences) with excitation at 640 nm and emission at 680 nm. The tumors were further fixed in 4% PFA with 10% sucrose in PBS overnight at 4° C. and embedded in Tissue-Tek® O.C.T. compound (Sakura Finetek USA, Inc.) for frozen sectioning (10 μm thick). The sectioned samples were mounted by ProLong® Gold Anti-fade Reagent with DAPI (Life Technologies) overnight. The fluorescent images were obtained using FluoView FV1000-Filter Confocal Microscope System (Olympus) (available at the University of Kentucky Markey Cancer Center Imaging core facility).

Assay for the Therapeutics Effect of RNA Nanoparticles on Regression of TNBC Cells in Animal Models When the tumor size reached about 5 mm in diameter, TNBC tumor bearing mice were randomly divided into two groups (N=12 each group). One group was injected with RNA nanoparticle 3WJ-EGFRapt/anti-miR-21 through tail vein over the course of 5 injections (Total RNA nanoparticle dose: 5 mg/kg; LNA dose: 0.26 mg/kg) every other day. PBS treated mice were served as treatment control. The tumor volume was measured and monitored every two days post injection, up to 15 days. The tumor volume was calculated as: (Length×width$^2$)/2. At the beginning and end of the injections, mice were subjected to bioluminescence whole body imaging to detect the endogenous luciferase expression level. Mice were anesthetized and intraperitoneally injected with 150 mg/kg D-luciferin (Biosynth International, Inc.). Bioluminescence from the anesthetized mice was detected by IVIS Spectrum station (Caliper Life Sciences). The mice were then sacrificed, tumors extracted and weighed followed by biochemical and histological analysis.

To quantify the miR-21 and subsequent target gene expression, the tumor tissues were flash frozen in liquid nitrogen and grounded using a mortar. The grounded tumor tissues were transferred to a clean centrifuge tube. Trizol RNA extraction reagent (Life Technologies) was added to extract the total RNA. Then, the miR-21 and subsequent target gene (PTEN and PDCD4) expression were quantified by qRT-PCR using Taqman Assays (Life Technologies) as described above.

Tumor tissues were also lysed in lysis buffer (2% SDS containing phosphatase and protease inhibitor cocktails) (Calbiochem) to quantify target gene expression at the protein level using Western Blot assay. Protein concentration was measured by BCA Protein Assay kit (Pierce). Equal amount of total protein was subjected to SDS-PAGE gel electrophoresis and transferred from gel to membrane. Membranes were blocked by 5% fat-free milk at room temperature for 1 hr and incubated overnight in primary antibody (PTEN, Cell Signaling, 1:1000; PDCD4, Cell Signaling, 1:1000; Lamin A/C, Santa Cruz, 1:1000). Protein bands were detected with an ECL system (Pierce) after incubating in the HRP-conjugated secondary antibody for 1 hr at room temperature and exposed to film for autoradiography.

The therapeutic effects of RNA nanoparticles were evaluated by histological profiling of Ki67 and caspase-3 activity in tumor tissues. Control and RNA nanoparticle treated group tumor sections were de-paraffined by incubating with xylene (10 minutes once, for three times), and hydrated from 100% ethanol, 95% ethanol, 85% ethanol and 70% ethanol to PBS solution. Slides were then incubated with 3% $H_2O_2$ for 20 min to block endogenous peroxidase. At the antigen retrieval step, the slides were steamed in 10 mM citrate sodium buffer (pH 6.0) for 30 min. All slides were blocked by 5% goat serum and Avidin/Biotin Blocking Kit (Vector labs). Then slides were incubated with primary antibodies (Ki67, Spring Bioscience, 1:500; Active caspase-3, Millipore, 1:100) at 4° C. overnight, and then the sections were incubated with goat anti-rabbit IgG conjugated with HRP at room temperature for 60 min. The conjugated antibody was detected by diaminobenzidine (DAB). All slides were counterstained with Hematoxylin and images were taken by Nikon microscope.

Statistical Analysis

Each experiment was repeated at least 3 times with duplication for each samples tested. The results were presented as mean±standard deviation, unless otherwise indicated. Statistical differences were evaluated using student's t-test, and $p<0.05$ was considered significant.

Throughout this document, various references are mentioned. All such references are incorporated herein by references, including the references set forth in the following list:

REFERENCES

1. Bartel, D. P. MicroRNAs: Genomics, Biogenesis, Mechanism, and Function. *Cell* 2004, 116, 281-297.
2. Liang, Z.; Wang, X. J. Rising From Ashes: Non-Coding RNAs Come of Age. *J Genet. Genomics* 2013, 40, 141-142.
3. Calin, G. A.; Croce, C. M. MicroRNA Signatures in Human Cancers. *Nat. Rev. Cancer* 2006, 6, 857-866.
4. Di, L. G.; Garofalo, M.; Croce, C. M. MicroRNAs in Cancer. *Annu. Rev. Pathol.* 2014, 9, 287-314.
5. Garzon, R.; Calin, G. A.; Croce, C. M. MicroRNAs in Cancer. *Annu. Rev. Med.* 2009, 60, 167-179.
6. Croce, C. M. Causes and Consequences of MicroRNA Dysregulation in Cancer. *Nat Rev. Genet.* 2009, 10, 704-714.
7. Iorio, M. V.; Ferracin, M.; Liu, C. G.; Veronese, A.; Spizzo, R.; Sabbioni, S.; Magri, E.; Pedriali, M.; Fabbri, M.; Campiglio, M.; et. al. MicroRNA Gene Expression Deregulation in Human Breast Cancer. *Cancer Res* 2005, 65, 7065-7070.
8. Croce, C. M.; Calin, G. A. MiRNAs, Cancer, and Stem Cell Division. *Cell* 2005, 122, 6-7
9. Kasinski, A. L.; Slack, F. J. Epigenetics and Genetics. MicroRNAs En Route to the Clinic: Progress in Validating and Targeting MicroRNAs for Cancer Therapy. *Nat. Rev. Cancer* 2011,11, 849-864.
10. Henry, J.; zevedo-Pouly, A.; Schmittgen, T. MicroRNA Replacement Therapy for Cancer. *Pharm Res* 2011, 28, 3030-3042.
11. Grodzinski, P.; Torchilin, V.; (Editors) *Adv. Drug Delivery Rev.: Cancer Nanotechnology*; Volume 66 ed.; Elsevier: 2014.

12. Peer, D.; Karp, J. M.; Hong, S.; Farokhzad, O. C.; Margalit, R.; Langer, R. Nanocarriers As an Emerging Platform for Cancer Therapy. *Nat Nanotechnol.* 2007, 2, 751-760.
13. Grodzinski, P.; Farrell, D. Future Opportunities in Cancer Nanotechnology—NCI Strategic Workshop Report. *Cancer Res.* 2014, 74, 1307-1310.
14. Guo, P. The Emerging Field of RNA Nanotechnology. *Nat. Nanotechnol.* 2010, 5, 833-842.
15. Foulkes, W. D.; Smith, I. E.; Reis-Filho, J. S. Triple-Negative Breast Cancer. *N. Engl. J Med.* 2010, 363, 1938-1948.
16. Fadare, O.; Tavassoli, F. A. Clinical and Pathologic Aspects of Basal-Like Breast Cancers. *Nat. Clin. Pract. Oncol.* 2008, 5, 149-159.
17. Guo, P.; Zhang, C.; Chen, C.; Trottier, M.; Garver, K. Inter-RNA Interaction of Phage Phi29 PRNA to Form a Hexameric Complex for Viral DNA Transportation. *Mol. Cell.* 1998, 2, 149-155.
18. Shu, Y.; Pi, F.; Sharma, A.; Rajabi, M.; Haque, F.; Shu, D.; Leggas, M.; Evers, B. M.; Guo, P. Stable RNA Nanoparticles As Potential New Generation Drugs for Cancer Therapy. *Adv. Drug Deliv. Rev.* 2014, 66C, 74-89.
19. Guo, P.; Haque, F.; Hallahan, B.; Reif, R.; Li, H. Uniqueness, Advantages, Challenges, Solutions, and Perspectives in Therapeutics Applying RNA Nanotechnology. *Nucleic Acid Ther.* 2012, 22, 226-245.
20. Lee, J. B.; Hong, J.; Bonner, D. K.; Poon, Z.; Hammond, P. T. Self-Assembled RNA Interference Microsponges for Efficient SiRNA Delivery. *Nat. Mater.* 2012, 11, 316-322.
21. Shopsowitz, K. E.; Roh, Y. H.; Deng, Z. J.; Morton, S. W.; Hammond, P. T. RNAi-Microsponges Form Through Self-Assembly of the Organic and Inorganic Products of Transcription. *Small* 2014, 10, 1623-1633.
22. Afonin, K. A.; Viard, M.; Koyfman, A. Y.; Martins, A. N.; Kasprzak, W. K.; Panigaj, M.; Desai, R.; Santhanam, A.; Grabow, W. W.; Jaeger, L.; et al. Multifunctional RNA Nanoparticles. *Nano Lett.* 2014, 14, 5662-5671.
23. Afonin, K. A.; Kireeva, M.; Grabow, W. W.; Kashlev, M.; Jaeger, L.; Shapiro, B. A. Co-Transcriptional Assembly of Chemically Modified RNA Nanoparticles Functionalized With SiRNAs. *Nano. Lett.* 2012, 12, 5192-5195.
24. Afonin, K. A.; Grabow, W. W.; Walker, F. M.; Bindewald, E.; Dobrovolskaia, M. A.; Shapiro, B. A.; Jaeger, L. Design and Self-Assembly of SiRNA-Functionalized RNA Nanoparticles for Use in Automated Nanomedicine. *Nat Protoc.* 2011, 6, 2022-2034.
25. Dibrov, S. M.; McLean, J.; Parsons, J.; Hermann, T. Self-Assembling RNA Square. *Proc. Natl. Acad. Sci. U. S. A* 2011, 108, 6405-6408.
26. Geary, C.; Rothemund, P. W.; Andersen, E. S. A Single-Stranded Architecture for Cotranscriptional Folding of RNA Nanostructures. *Science* 2014, 345, 799-804.
27. Han, D.; Park, Y.; Kim, H.; Lee, J. B. Self-Assembly of Free-Standing RNA Membranes. *Nat. Commun.* 2014, 5.
28. Lee, T. J.; Haque, F.; Shu, D.; Yoo, J. Y.; Li, H.; Yokel, R. A.; Horbinski, C.; Kim, T. H.; Kim, S.-H.; Nakano, I.; Kaur, B.; Croce, C. M.; Guo, P. RNA Nanoparticles As a Vector for Targeted SiRNA Delivery into Glioblastoma Mouse Model. *Oncotarget* 2015, (In Press).
29. Li, H.; Rychahou, P. G.; Cui, Z.; Pi, F.; Evers, B. M.; Shu, D.; Guo, P.; Luo, W. RNA Nanoparticles Derived From Three-Way Junction of Phi29 Motor PRNA Are Resistant to 1-125 and Cs-131 Radiation. *Nucleic Acid Ther.* 2015.
30. Zhang, Y.; Wang, Z.; Gemeinhart, R. A. Progress in MicroRNA Delivery. *J Control Release* 2013, 172, 962-974.
31. Griveau, A.; Bejaud, J.; Anthiya, S.; Avril, S.; Autret, D.; Garcion, E. Silencing of MiR-21 by Locked Nucleic Acid-Lipid Nanocapsule Complexes Sensitize Human Glioblastoma Cells to Radiation-Induced Cell Death. *Int. J Pharm.* 2013, 454, 765-774.
32. Takahashi, M.; Yamada, N.; Hatakeyama, H.; Murata, M.; Sato, Y.; Minakawa, N.; Harashima, H.; Matsuda, A. In vitro Optimization of 2'-OMe-4'-Thioribonucleoside-Modified Anti-MicroRNA Oligonucleotides and Its Targeting Delivery to Mouse Liver Using a Liposomal Nanoparticle. *Nucleic Acids Res* 2013, 41, 10659-10667.
33. Hatakeyama, H.; Murata, M.; Sato, Y.; Takahashi, M.; Minakawa, N.; Matsuda, A.; Harashima, H. The Systemic Administration of an Anti-MiRNA Oligonucleotide Encapsulated PH-Sensitive Liposome Results in Reduced Level of Hepatic MicroRNA-122 in Mice. *J Control Release* 2013.
34. Cheng, C. J.; Saltzman, W. M. Polymer Nanoparticle-Mediated Delivery of MicroRNA Inhibition and Alternative Splicing. *Mol Pharm.* 2012, 9, 1481-1488.
35. Babar, I. A.; Cheng, C. J.; Booth, C. J.; Liang, X.; Weidhaas, J. B.; Saltzman, W. M.; Slack, F. J. Nanoparticle-Based Therapy in an in vivo MicroRNA-155 (MiR-155)-Dependent Mouse Model of Lymphoma. *Proc. Natl. Acad. Sci. U. S A* 2012, 109, E1695-E1704.
36. Kim, J. H.; Yeom, J. H.; Ko, J. J.; Han, M. S.; Lee, K.; Na, S. Y.; Bae, J. Effective Delivery of Anti-MiRNA DNA Oligonucleotides by Functionalized Gold Nanoparticles. *J Biotechnol.* 2011, 155, 287-292.
37. Liu, J.; Guo, S.; Cinier, M.; Shlyakhtenko, L. S.; Shu, Y.; Chen, C.; Shen, G.; Guo, P. Fabrication of Stable and RNase-Resistant RNA Nanoparticles Active in Gearing the Nanomotors for Viral DNA Packaging. *ACS Nano* 2011, 5, 237-246.
38. Shu, D.; Shu, Y.; Haque, F.; Abdelmawla, S.; Guo, P. Thermodynamically Stable RNA Three-Way Junctions for Constructing Multifuntional Nanoparticles for Delivery of Therapeutics. *Nat. Nanotechnol.* 2011, 6, 658-667.
39. Haque, F.; Shu, D.; Shu, Y.; Shlyakhtenko, L.; Rychahou, P.; Evers, M.; Guo, P. Ultrastable Synergistic Tetravalent RNA Nanoparticles for Targeting to Cancers. *Nano Today* 2012, 7, 245-257.
40. Binzel, D. W.; Khisamutdinov, E. F.; Guo, P. Entropy-Driven One-Step Formation of Phi29 PRNA 3WJ From Three RNA Fragments. *Biochemistry* 2014, 53, 2221-2231.
41. Khisamutdinov, E.; Li, H.; Jasinski, D.; Chen, J.; Fu, J.; Guo, P. Enhancing Immunomodulation on Innate Immunity by Shape Transition Among RNA Triangle, Square, and Pentagon Nanovehicles. *Nucelic Acids Research* 2014, 42, 9996-10004.
42. Abdelmawla, S.; Guo, S.; Zhang, L.; Pulukuri, S.; Patankar, P.; Conley, P.; Trebley, J.; Guo, P.; Li, Q. X. Pharmacological Characterization of Chemically Synthesized Monomeric PRNA Nanoparticles for Systemic Delivery. *Mol. Ther.* 2011, 19, 1312-1322.
43. Hunter, M. P.; Ismail, N.; Zhang, X.; Aguda, B. D.; Lee, E. J.; Yu, L.; Xiao, T.; Schafer, J.; Lee, M. L. T.; Schmittgen, T. D.; et al. Detection of MicroRNA Expression in Human Peripheral Blood Microvesicles. *PLoS ONE* 2008, 3, e3694.
44. Srivastava, A.; Filant, J.; Moxley, K. M.; Sood, A.; McMeekin, S.; Ramesh, R. Exosomes: A Role for Naturally Occurring Nanovesicles in Cancer Growth, Diagnosis and Treatment. *Current gene therapy* 2014.
45. Zhang, H. G.; Grizzle, W. E. Exosomes: A Novel Pathway of Local and Distant Intercellular Communication That Facilitates the Growth and Metastasis of Neoplastic Lesions. *The American journal of pathology* 2014, 184, 28-41.
46. Redzic, J. S.; Balaj, L.; van der Vos, K. E.; Breakefield, X. O. Extracellular RNA Mediates and Marks Cancer Progression. *Semin. Cancer Biol.* 2014, 28, 14-23.
47. Eldh, M.; Olofsson Bagge, R.; Lasser, C.; Svanvik, J.; Sjostrand, M.; Mattsson, J.; Lindner, P.; Choi, D. S.; Gho, Y.; Lotvall, J. MicroRNA in Exosomes Isolated Directly From the Liver Circulation in Patients With Metastatic Uveal Melanoma. *BMC Cancer* 2014, 14, 962.
48. Shu, Y.; Haque, F.; Shu, D.; Li, W.; Zhu, Z.; Kotb, M.; Lyubchenko, Y.; Guo, P. Fabrication of 14 Different RNA Nanoparticles for Specific Tumor Targeting Without Accumulation in Normal Organs. RNA 2013, 19, 766-777.
49. Zhang, H.; Endrizzi, J. A.; Shu, Y.; Haque, F.; Sauter, C.; Shlyakhtenko, L. S.; Lyubchenko, Y.; Guo, P.; Chi, Y. I. Crystal Structure of 3WJ Core Revealing Divalent Ion-Promoted Thermostability and Assembly of the Phi29 Hexameric Motor PRNA. RNA 2013, 19, 1226-1237.
50. Guo, P.; Erickson, S.; Anderson, D. A Small Viral RNA Is Required for in vitro Packaging of Bacteriophage Phi29 DNA. *Science* 1987, 236, 690-694.
51. Esposito, C. L.; Passaro, D.; Longobardo, I.; Condorelli, G.; Marotta, P.; Affuso, A.; de, F., V; Cerchia, L. A Neutralizing RNA Aptamer Against EGFR Causes Selective Apoptotic Cell Death. *PLoS ONE* 2011, 6, e24071.
52. Hynes, N. E.; Lane, H. A. ERBB Receptors and Cancer: the Complexity of Targeted Inhibitors. *Nat Rev. Cancer* 2005, 5, 341-354.
53. Pantel, K.; Brakenhoff, R. H.; Brandt, B. Detection, Clinical Relevance and Specific Biological Properties of Disseminating Tumour Cells. *Nat Rev. Cancer* 2008, 8, 329-340.
54. Zhu, S.; Si, M. L.; Wu, H.; Mo, Y. Y. MicroRNA-21 Targets the Tumor Suppressor Gene Tropomyosin 1 (TPM1). *J. Biol Chem.* 2007, 282, 14328-14336.
55. Frankel, L. B.; Christoffersen, N. R.; Jacobsen, A.; Lindow, M.; Krogh, A.; Lund, A. H. Programmed Cell Death 4 (PDCD4) Is an Important Functional Target of the MicroRNA MiR-21 in Breast Cancer Cells. *J. Biol Chem.* 2008, 283, 1026-1033.
56. Qi, L.; Bart, J.; Tan, L. P.; Platteel, I.; Sluis, T.; Huitema, S.; Harms, G.; Fu, L.; Hollema, H.; Berg, A. Expression of MiR-21 and Its Targets (PTEN, PDCD4, TM1) in Flat Epithelial Atypia of the Breast in Relation to Ductal Carcinoma in situ and Invasive Carcinoma. *BMC. Cancer* 2009, 9, 163.
57. Zhu, S.; Wu, H.; Wu, F.; Nie, D.; Sheng, S.; Mo, Y. Y. MicroRNA-21 Targets Tumor Suppressor Genes in Invasion and Metastasis. *Cell Res* 2008, 18, 350-359.
58. Si, M. L.; Zhu, S.; Wu, H.; Lu, Z.; Wu, F.; Mo, Y. Y. MiR-21-Mediated Tumor Growth. *Oncogene* 2007, 26, 2799-2803.
59. Shu, D.; Zhang, L.; Khisamutdinov, E.; Guo, P. Programmable Folding of Fusion RNA Complex Driven by the 3WJ Motif of Phi29 Motor PRNA. *Nucleic Acids Res.* 2013, 42, e10.
60. Behlke, M. A. Chemical Modification of siRNAs for in vivo Use. *Oligonucleotides.* 2008, 18, 305-319.
61. Mathe, C.; Perigaud, C. Recent Approaches in the Synthesis of Conformationally Restricted Nucleoside Analogues. *Eur. J. Org. Chem.* 2008, 1489-1505.
62. Jasinski, D.; Khisamutdinov, E. F.; Lyubchenko, Y. L.; Guo, P. Physicochemically Tunable Poly-Functionalized RNA Square Architecture With Fluorogenic and Ribozymatic Properties. *ACS Nano* 2014, 8, 7620-7629.
63. Khisamutdinov, E. F.; Jasinski, D. L.; Guo, P. RNA As a Boiling-Resistant Anionic Polymer Material to Build Robust Structures With Defined Shape and Stoichiometry. *ACS Nano.* 2014, 8, 4771-4781.
64. Obad, S.; dos Santos, C. O.; Petri, A.; Heidenblad, M.; Broom, O.; Ruse, C.; Fu, C.; Lindow, M.; Stenvang, J.; Straarup, E. M.; et al. Silencing of MicroRNA Families by Seed-Targeting Tiny LNAs. *Nat. Genet.* 2011, 43, 371-378.
65. Castoldi, M.; Schmidt, S.; Benes, V.; Hentze, M. W.; Muckenthaler, M. U. MiChip: an Array-Based Method for MicroRNA Expression Profiling Using Locked Nucleic Acid Capture Probes. *Nat Protoc.* 2008, 3, 321-329.
66. Fire, A.; Xu, S.; Montgomery, M. K.; Kostas, S. A.; Driver, S. E.; Mello, C. C. Potent and Specific Genetic Interference by Double-Stranded RNA in *Caenorhabditis Elegans*. *Nature* 1998, 391, 806-811.
67. Wu, S. Y.; Lopez-Berestein, G.; Calin, G. A.; Sood, A. K. RNAi Therapies: Drugging the Undruggable. *Sci. Transl. Med.* 2014, 6, 240ps7.
68. Tabernero, J.; Shapiro, G. I.; Lorusso, P. M.; Cervantes, A.; Schwartz, G. K.; Weiss, G. J.; Paz-Ares, L.; Cho, D. C.; Infante, J. R.; Alsina, M.; et al. First-in-Man Trial of an RNA Interference Therapeutic Targeting VEGF and KSP in Cancer Patients With Liver Involvement. *Cancer Discov.* 2013, 3, 406-417.
69. Bora, R. S.; Gupta, D.; Mukkur, T. K.; Saini, K. S. RNA Interference Therapeutics for Cancer: Challenges and Opportunities (Review). *Mol. Med.* Rep. 2012, 6, 9-15.
70. Tiemann, K.; Rossi, J. J. RNAi-Based Therapeutics-Current Status, Challenges and Prospects. *EMBO Mol. Med.* 2009, 1, 142-151.
71. Aagaard, L.; Rossi, J. J. RNAi Therapeutics: Principles, Prospects and Challenges. *Adv. Drug Delivery Rev.* 2007, 59, 75-86.
72. Bumcrot, D.; Manoharan, M.; Koteliansky, V.; Sah, D. W. RNAi Therapeutics: a Potential New Class of Pharmaceutical Drugs. *Nat Chem. Biol.* 2006, 2, 711-719.
73. Robinson, R. RNAi Therapeutics: How Likely, How Soon? *Plos Biology* 2004, 2, e28.
74. Morrissey, D. V.; Lockridge, J. A.; Shaw, L.; Blanchard, K.; Jensen, K.; Breen, W.; Hartsough, K.; Machemer, L.; Radka, S.; Jadhav, V.; et al. Potent and Persistent in vivo Anti-HBV Activity of Chemically Modified siRNAs. *Nat. Biotechnol.* 2005, 23, 1002-1007.
75. Longmire, M.; Choyke, P. L.; Kobayashi, H. Clearance Properties of Nano-Sized Particles and Molecules As Imaging Agents: Considerations and Caveats. Nanomedicine (Lond) 2008, 3, 703-717.
76. Lyubchenko, Y. L.; Shlyakhtenko, L. S.; Ando, T. Imaging of Nucleic Acids With Atomic Force Microscopy. *Methods* 2011, 54, 274-283.
77. Lyubchenko, Y. L.; Shlyakhtenko, L. S. AFM for Analysis of Structure and Dynamics of DNA and Protein-DNA Complexes. *Methods* 2009, 47, 206-213.
78. Lyubchenko, Y. L.; Gall, A. A.; Shlyakhtenko, L. S.; Harrington, R. E.; Jacobs, B. L.; Oden, P. I.; Lindsay, S. M. Atomic Force Microscopy Imaging of Double Stranded DNA and RNA. *J. Biomol. Struct. Dyn.* 1992, 10, 589-606.

79. Abels, J. A.; Moreno-Herrero, F.; van der Heijden, T.; Dekker, C. F.; Dekker, N. H. Single-Molecule Measurements of the Persistence Length of Double-Stranded RNA. *Biophys. J.* 2005, 88, 2737-2744.

What is claimed is:

1. An artificial RNA nanostructure molecule, comprising: a multiple branched RNA junction motif comprising at least one RNA oligonucleotides, and a breast cancer targeting module coupled to the RNA junction motif, 5'-UUG CCA UGU GUA UGU GGG AUC CCG CGG CCA UGG CGG CCG GGA G-3' (SEQ ID NO: 5).

2. The molecule of claim 1, further comprising at least one bioactive agent coupled to the RNA junction motif.

3. The molecule of claim 1, wherein the bioactive agent is a therapeutic agent.

4. The molecule of claim 1, wherein the RNA oligonucleotide comprises at least one chemical modification at the 2' position.

5. The molecule of claim 1, wherein the modification comprises 2'Fluoro, 2'Amine, or 2'O-Methyl.

6. The molecule of claim 1, wherein the multiple branched RNA junction motif is a three-branched RNA junction motif.

7. The molecule of claim 1, wherein the multiple branched RNA further comprises sequence 5'-CCC ACA UAC UUU GUU GAU CCG CCU UAG UAA CGU GCU UUG AUG UCG AUU CGA CAG GAG GC-3'(SEQ ID NO: 6); 5'-GATAAGCT CTC CCG GCC GCC ATG GCC GCG GGA T-3' (SEQ ID NO: 7); 5'-CTC CCG GCC GCC ATG GCC GCG GGA T-3' (SEQ ID NO: 8); 5'-AUC CCG CGG CCA UGG CGG CCG GGA G-3' (SEQ ID NO: 9); or a combination thereof.

8. The molecule of claim 1, wherein the diameter of the molecule is at least about 40 nm or less.

9. The molecule of claim 1, wherein the molecule has zeta potential ranging from about −100 mV to about 100 mV.

10. The molecule of claim 6, wherein a branch of the three-branched RNA junction motif comprises an a 3WJ RNA module (SEQ ID NO: 1); a b3WJ RNA module (SEQ ID NO: 2); or a c3WJ RNA module (SEQ ID NO: 3).

11. The molecule of claim 6, wherein the three-branched RNA junction motif comprises an a 3WJ RNA module (SEQ ID NO: 1); a b3WJ RNA module (SEQ ID NO: 2); and a c3WJ RNA module (SEQ ID NO: 3).

12. The molecule of claim 1, wherein the breast cancer targeting module comprises a ligand that binds to at least one breast cancer cell surface marker.

13. The molecule of claim 12, wherein the ligand binds to a folate receptor, an epidermal growth factor receptor 2 (ErbB-2/HER2), an epidermal growth factor receptor (EGFR), a HER2, or a combination thereof.

14. The molecule of claim 12, wherein the ligand is an aptamer.

15. The molecule of claim 14, wherein the aptamer binds to EGFR, PDGFR, folate receptor, or a combination thereof.

16. The molecule of claim 14, wherein the ligand is a EGFR targeting aptamer.

17. The molecule of claim 1, wherein the ligand has sequence 5'-G CCU UAG UAA CGU GCU UUG AUG UCG AUU CGA CAG GAG GC-3'(SEQ ID NO: 10).

18. The molecule of claim 1, wherein the targeting module is a folate.

19. The molecule of claim 18, wherein the folate is folic acid, 5-methyltetrahydro folate, 5-formyltetrahydrofolate, dihydrofolate, tetrahydrofolate, or a combination thereof.

20. The molecule of claim 2, wherein the bioactive agent is a drug, a fluorescent dye, or a chemical, or a combination thereof.

21. The molecule of claim 2, wherein the bioactive agent is a siRNA, a miRNA, an anti-miRNA, a ribozyme RNAs, or an antisense RNA.

22. The molecule of claim 2, wherein the bioactive agent is directed to a breast cancer marker.

23. The molecule of claim 21, wherein the bioactive agent is a siRNA sequence or a microRNA sequence.

24. The molecule of claim 21, wherein the bioactive agent is a miRNA molecule for a miRNA comprising miR-9, miR-10b, miR-21, miR-17, miR-26, let-7a, miR-25, miR-34a, miR-124, miR-145, or miR-181b.

25. The molecule of claim 21, wherein the microRNA sequence is an anti-miR-21 sequence.

26. The molecule of claim 25, wherein the anti-miR-21 sequence comprises 5'-GATAAGCT-3' (SEQ ID NO: 11).

27. The molecule of claim 25, wherein the anti-miRNA comprises an anti-miRNA locked nucleic acid (LNA) molecule.

28. The molecule of claim 21, wherein the anti-miRNA LNA molecule comprises sequence 5'-GATAAGCT-3', 5'-AGCACTTT-3', or 5'-ATTTGCAC-3'.

29. The molecule of claim 23, wherein the siRNa binds to a mRNA molecule that encodes RAS, cMET, HER2, MDM2, PIK3CA, AKT, CDK4, or a combination thereof.

30. The molecule of claim 1, wherein the RNA nanostructure inhibit breast cancer cells proliferation.

31. A nucleic acid composition, comprising a therapeutically effective amount of the RNA nanostructure of claim 1 and a pharmaceutically acceptable carrier.

32. A nanoparticle delivery system, comprising a RNA nanostructure of claim 1 and a pharmaceutically acceptable carrier.

33. A method of treating a breast tumor in a subject having or at risk of developing a breast cancer, the method comprising administering to the subject a therapeutically effective amount of a composition comprising a molecule of claim 1 and a pharmaceutically acceptable carrier.

34. The method of claim 33, wherein the breast cancer is triple negative breast cancer.

* * * * *

UNITED STATES PATENT AND TRADEMARK OFFICE
CERTIFICATE OF CORRECTION

| | |
|---|---|
| PATENT NO. | : 11,085,044 B2 |
| APPLICATION NO. | : 15/555822 |
| DATED | : August 10, 2021 |
| INVENTOR(S) | : Guo et al. |

It is certified that error appears in the above-identified patent and that said Letters Patent is hereby corrected as shown below:

In the Specification

Replace the second paragraph, which appears on Column 1, with the following:
Government Interest
This invention was made with government support under EB019036, CA 151648 and EB0037305 awarded by the National Institutes of Health, and under W81XWH-15-1-0052 awarded by the Department of Defense. The government has certain rights in the invention.

Signed and Sealed this
Thirty-first Day of January, 2023

Katherine Kelly Vidal
*Director of the United States Patent and Trademark Office*